US012768788B2

United States Patent
(12) United States Patent
Lim et al.

(10) Patent No.: US 12,768,788 B2
(45) Date of Patent: Oct. 20, 2026

(54) ANALYSIS OF EMBEDDED TISSUE SAMPLES USING FLUORESCENCE-BASED DETECTION

(71) Applicant: Agilent Technologies, Inc., Santa Clara, CA (US)

(72) Inventors: Victor Lim, Pacifica, CA (US); Adrienne McCampbell, San Jose, CA (US); Qingyu Wang, Los Altos, CA (US)

(73) Assignee: AGILENT TECHNOLOGIES, INC., Santa Clara, CA (US)

(*) Notice: Subject to any disclaimer, the term of this patent is extended or adjusted under 35 U.S.C. 154(b) by 465 days.

(21) Appl. No.: 18/261,751

(22) PCT Filed: Dec. 30, 2021

(86) PCT No.: PCT/US2021/065722
§ 371 (c)(1),
(2) Date: Jul. 17, 2023

(87) PCT Pub. No.: WO2022/164568
PCT Pub. Date: Aug. 4, 2022

(65) Prior Publication Data
US 2024/0102932 A1 Mar. 28, 2024

Related U.S. Application Data

(60) Provisional application No. 63/144,372, filed on Feb. 1, 2021.

(51) Int. Cl.
*G01N 21/64* (2006.01)
*G01N 1/06* (2006.01)
(Continued)

(52) U.S. Cl.
CPC .......... *G01N 21/6458* (2013.01); *G01N 1/06* (2013.01); *G01N 21/6486* (2013.01);
(Continued)

(58) Field of Classification Search
CPC .. G01N 21/6458; G01N 1/06; G01N 21/6486; G01N 2201/126; G01N 1/36;
(Continued)

(56) References Cited

U.S. PATENT DOCUMENTS 10,269,094 B2 4/2019 Fuchs
10,671,832 B2 6/2020 Hamilton
(Continued)

FOREIGN PATENT DOCUMENTS

CN 104520689 A 4/2015
CN 107003242 A 8/2017
(Continued)

OTHER PUBLICATIONS

Office Action issued in Japanese Patent Application No. 2023-546139, dated Oct. 3, 2025 (with machine translation).
(Continued)

*Primary Examiner* — Ming Y Hon

(57) ABSTRACT

The present disclosure is directed to an improved methods and systems using autofluorescence of naturally-occurring components in a sample embedded in an embedding medium. Methods and systems are provided for determining an amount of tissue or cell preparation exposed at a surface of an embedded sample, and for preparing a tissue specimen comprising a region of interest (ROI) from an embedded sample. Methods and systems are also provided for imaging a sample of a biological tissue, and for identifying different cell types in an embedded tissue sample.

11 Claims, 10 Drawing Sheets

(51) Int. Cl.

| | |
|---|---|
| ***G06V 10/25*** | (2022.01) |
| ***G06V 10/774*** | (2022.01) |
| ***G06V 10/82*** | (2022.01) |
| ***G06V 20/69*** | (2022.01) |
| ***G16H 30/40*** | (2018.01) |

(52) U.S. Cl.
CPC ............ *G06V 10/25* (2022.01); *G06V 10/774* (2022.01); *G06V 10/82* (2022.01); *G06V 20/698* (2022.01); *G16H 30/40* (2018.01); *G01N 2201/126* (2013.01)

(58) Field of Classification Search
CPC ........... G01N 2201/1296; G06V 10/25; G06V 10/774; G06V 10/82; G06V 20/698; G16H 30/40; G06N 3/0464; G06N 3/09; G06N 3/045; G06N 3/08
See application file for complete search history.

(56) References Cited

U.S. PATENT DOCUMENTS

| | | | |
|---|---|---|---|
| 10,684,199 B2 | 6/2020 | Schleifer et al. | |
| 10,914,658 B2 | 2/2021 | Schleifer et al. | |
| 11,467,071 B2 | 10/2022 | Mitra et al. | |
| 2004/0026630 A1 | 2/2004 | Mohun et al. | |
| 2006/0146346 A1 | 7/2006 | Hoyt | |
| 2009/0091566 A1 | 4/2009 | Turney et al. | |
| 2009/0220130 A1 | 9/2009 | Slingerland | |
| 2010/0118133 A1 | 5/2010 | Walter et al. | |
| 2012/0002043 A1 | 1/2012 | Nitta | |
| 2013/0023008 A1 | 1/2013 | Becker et al. | |
| 2015/0050650 A1 | 2/2015 | Seppo et al. | |
| 2015/0141278 A1 | 5/2015 | Hollman-Hewgley et al. | |
| 2015/0196202 A1* | 7/2015 | Mercader | A61B 1/043 600/478 |
| 2016/0278678 A1* | 9/2016 | Valdes | A61B 5/14556 |
| 2016/0290926 A1 | 10/2016 | Notingher et al. | |
| 2016/0313224 A1 | 10/2016 | Lau et al. | |
| 2017/0191937 A1 | 7/2017 | Levenson et al. | |
| 2018/0028079 A1* | 2/2018 | Gurevich | A61B 5/7232 |
| 2018/0120207 A1 | 5/2018 | Lim et al. | |
| 2018/0231548 A1* | 8/2018 | Bradley | A61K 49/0021 |
| 2019/0087688 A1* | 3/2019 | Peng | G16H 50/30 |
| 2019/0188446 A1 | 6/2019 | Wu et al. | |
| 2019/0301980 A1 | 10/2019 | Anderson et al. | |
| 2019/0339203 A1* | 11/2019 | Miller | G01N 21/6456 |
| 2019/0368982 A1* | 12/2019 | Schleifer | G01N 1/06 |
| 2020/0264077 A1 | 8/2020 | Schleifer et al. | |
| 2020/0367818 A1* | 11/2020 | DaCosta | A61B 90/30 |
| 2021/0108995 A1 | 4/2021 | Schleifer et al. | |
| 2023/0047584 A1* | 2/2023 | Bruza | G01S 17/89 |
| 2025/0251402 A1* | 8/2025 | Dubach | G01N 33/533 |

FOREIGN PATENT DOCUMENTS

| | | | |
|---|---|---|---|
| CN | 109307662 | A | 2/2019 |
| EP | 0209369 | A2 | 1/1987 |
| JP | 2004515780 | A | 5/2004 |
| JP | 2009517665 | A | 4/2009 |
| JP | F 2010044069 | A | 2/2010 |
| JP | F 2010230495 | A | 10/2010 |
| JP | 2015514213 | A | 5/2015 |
| JP | 2015516847 | A | 6/2015 |
| JP | 2016517985 | A | 6/2016 |
| JP | 2019-028062 | A | 2/2019 |
| WO | 0248692 | A1 | 6/2002 |
| WO | 2007062444 | A1 | 6/2007 |
| WO | 2013152395 | A1 | 10/2013 |
| WO | 2014172530 | A1 | 10/2014 |
| WO | 2018157074 | A1 | 8/2018 |
| WO | WO 2020/161125 | A1 | 8/2020 |

OTHER PUBLICATIONS

Epo, et al., "Partial European Search Report (R.164 EPC) mailed on Nov. 28, 2024," Application No. 21923573.6, 12 pages.

Saif, Mari et al.,"Non-invasive monitoring of chronic liver disease via near-infrared and shortwave-infrared imaging of endogenous lipofuscin," Nature Biomedical Engineering, vol. 4, No. 8, XP037368083, DOI: 10.1038/S41551-020-0569-Y, Aug. 2020, 801-813.

Office Action issued in Japanese Patent Application No. 2023-546139, dated Mar. 27, 2026.

Office Action issued in Australian Patent Application No. 2021424678, dated Jan. 15, 2026.

Davis, A. S. et al., "Characterizing and Diminishing Autofluorescence in Formalin-Fixed Paraffin-Embedded Human Respiratory Tissue," Journal of Histochemistry & Cytochemistry, vol. 62, No. 6, 2014, 405-423.

EPO, "Extended European Search Report mailed on Oct. 8, 2018," Application No. 18184642.9, 9 pages.

PCT, "Notification of Transmittal of The International Search Report & Written Opinion mailed on Apr. 22, 2022," Application No. PCT/US2021/065722, Apr. 22, 2022, 11 pages.

Elozory, D. T. et al., "Automatic section thickness determination using an absolute gradient focus function," Journal of Microscopy, 248.3 (2012): 245-259.

Office Action issued in Chinese Patent Application No. 202180092674.7, dated Jun. 16, 2026.

* cited by examiner

ANALYSIS OF EMBEDDED TISSUE SAMPLES USING FLUORESCENCE-BASED DETECTION

CROSS-REFERENCE TO RELATED APPLICATIONS

This application is a US national stage entry of PCT/US2021/065722, filed Dec. 30, 2021, which claims the benefit of U.S. Patent Application No. 63/144,372, filed on Feb. 1, 2021, the contents of which are incorporated herein by reference in their entirety.

FIELD OF THE INVENTION

The present disclosure relates to analysis of embedded tissue samples such as a formalin-fixed paraffin-embedded sample, using fluorescence-based detection, automated tissue section preparation, and artificial intelligence.

BACKGROUND

The formation of a formalin-fixed paraffin-embedded (FFPE) tissue block serves to preserve the morphology and cellular content of a tissue sample. Tissue processing generally involves placing an isolated tissue in formalin for a time period such as a few days, and then embedding the tissue in a paraffin wax. FETE samples can be conveniently stored at room temperature for extended periods of time and are especially useful for immunohistochemical staining and morphology analyses. FFPE samples may also be used for profiling gene expression and studying diseases.

At the time of biological testing, the FETE tissue block is generally trimmed by cutting the tissue block on a microtome. The tissue block may be analyzed to determine the boundaries of the tissue in the FFPE by a technician or using an automated method. In the former case, a technician generally examines the FFPE block to observe the diffuse image of the tissue embedded in the paraffin. The technician may ascertain what the cross-sectional area of a section comprising the tissue should look like and compare that to the tissue sections as they emerge from the microtome blade. Preferably, the tissue block is trimmed to expose a representative amount of tissue to the surface of the block and to ensure that the block face is in line with the knife's edge.

During automated analysis, a camera is commonly utilized to image the tissue. A light source illuminates the surface of the tissue block at an angle to distinguish the difference between the paraffin and tissue surfaces. Since paraffin is comparably smoother than tissue, automated analysis utilizes the different natural textures of paraffin and tissue to differentiate between the two materials.

Many existing methods provide inaccurate and inconsistent data when used to analyze different tissue and paraffin types, since such methods are sensitive to variability of optical and surface characteristics of tissue and paraffin. In some cases, it is quite difficult to distinguish tissue from paraffin in an FFPE sample using existing methods.

Following microtomy from the tissue block, the tissue section is mounted to a slide by smoothing the tissue section in a water bath and baking it. Hematoxylin and Eosin (ME) staining is performed and the tissue section is reviewed by a pathologist. During the pathologist review of an H&E stained tissue section suspected to contain cancer cells, they will identify which cells are cancerous amongst the surrounding benign cells which can consist of stroma, fibroblasts, blood vessels, and extracellular matrix. Tumor cells can have larger nuclei compared to normal cells of the same origin or compared to the many other cell types present including those in the extracellular matrix. Extracellular matrix and normal cell types tend to have much higher levels of collagen and elastin compared to tumor cells.

The identification of mutations in tumors allows for pathologists and oncologists to direct patient prognosis and therapy. Oncogenes are genes that in a normal cell promote protein production to stimulate normal growth of cells. Presence of mutations in oncogenes promotes unsuppressed growth and proliferation of tumor cells. Tumor suppressor genes are genes that normally function to inhibit over-proliferation of proteins in normal cells. Mutations in tumor suppressor genes promote increased growth and proliferation of tumor cells. Drugs have been developed for tumors having certain mutations in oncogenes or tumor suppressors. The immune response role in cancer also indicates that mutations in other regulatory pathways can be targeted by drug therapy.

For the identification of mutations in tumor cells, there is preferably a tumor content of 20% or greater for the success of quantitative polymerase chain reaction (qPCR) and other next generation sequencing (NGS) tests, methods used to identify mutations. Macro-dissection is a tumor enrichment method whereby the pathologist carefully selects regions of interest (ROI) that preferably contain greater than 20% tumor content. The pathologist draws a circle around the region with a marker on the top of the H&E stained section. A technician then uses multiple unstained HIT tissue sections mounted onto slides to select the ROI identified by the pathologist. The technician typically scrapes the tissue in the ROI off of the slide and places it into a centrifuge tube. DNA from the scraped tissue is isolated for NGS testing. Macro-dissection requires significant time from the pathologists, as it is very time consuming to sit at a bright field microscope to evaluate multiple slides to find the best example with high tumor content and then manually circle ROIs.

Nuclear segmentation in digital microscopic tissue images can enable extraction of high-quality features for nuclear morphometric and other analyses in computational pathology. However, conventional image processing techniques such as Otsu and watershed segmentation do not work effectively on challenging cases such as chromatin-sparse and crowded nuclei. In contrast, machine learning-based segmentation techniques are effective over a more general set of nuclear appearances. However, training machine learning algorithms requires large image datasets in which a vast number of nuclei must be been annotated. Typically, a large publicly accessible dataset of H&E stained tissue images with painstakingly annotated nuclear boundaries are used for nuclear segmentation algorithm development. An informative dataset should include a diversity of nuclear appearances from several patients, disease states, and organs, and techniques trained on it are likely to generalize well and work right out-of-the-box on novel H&E stained images.

Accordingly, there is a need for additional methods and apparatus for determining a region of interest in a tissue sample in an embedding medium, and to facilitate the efficient preparation of useful tissue sections from the embedded sample.

SUMMARY OF THE INVENTION

As an aspect of the present invention, a method is provided for determining an amount of a tissue or a cell preparation exposed at a surface of a sample embedded in an embedding medium such as paraffin. The method comprises irradiating the embedded tissue or cell preparation sample at a wavelength which causes endogenous components of the tissue to autofluoresce; obtaining an image of the autofluorescence emitted by the embedded tissue or cell preparation sample; and determining a percentage of the image at the surface of the embedding medium which is occupied by tissue or cell preparation.

As another aspect of the present invention, a method is provided for identifying different cell types in an embedded tissue sample. The method comprises irradiating the embedded tissue sample at a wavelength which causes endogenous components of a tissue to autofluoresce; obtaining an image of the autofluorescence emitted by the tissue sample; and identifying different cell types in the image of the autofluorescence emitted by the tissue sample based upon autofluorescence characteristics.

As another aspect of the present invention, a method is provided for training an artificial intelligence (AI) system to identify a region of interest (ROI) in an embedded tissue sample comprising a tissue and an embedding medium. The method comprises irradiating the embedded tissue sample at a wavelength which causes endogenous components of the tissue to autofluoresce; obtaining an image of the autofluorescence emitted by the embedded tissue sample; annotating the image to indicate the ROIs in the image; and inputting the annotated image into the AI system, wherein the AI system learns to identify ROIs in unannotated images.

As another aspect of the present invention, a method is provided for preparing a tissue specimen comprising a region of interest (ROI) from an embedded sample. The method comprises obtaining a trained AI system adapted for identifying the ROI from an unstained embedded sample; irradiating the embedded sample comprising a tissue and an embedding medium with electromagnetic radiation having an excitation wavelength; generating a fluorescence image of the embedded sample; using the trained AI system to identify the ROI in the embedded sample based on the fluorescence image and without staining the embedded sample; and collecting a portion of the embedded sample identified as having the ROI as the tissue specimen.

As another aspect of the present invention, a method is provided for imaging a sample of a biological tissue. The method comprises irradiating a biological tissue sample at an excitation wavelength which causes endogenous components of the biological tissue to autofluoresce; obtaining an image of the autofluorescence emitted by the biological tissue sample to identify regions of the biological tissue comprising extracellular matrix; and staining nuclei in the biological tissue sample with a nuclear stain to identify regions of the biological tissue comprising cellular nuclei.

The present invention also comprises apparatus configured to perform the various steps of the methods described herein.

These and other features and advantages of the present methods and apparatus will be apparent from the following detailed description, in conjunction with the appended claims.

BRIEF DESCRIPTION OF THE DRAWINGS

The present teachings are best understood from the following detailed description when read with the accompanying drawing figures. The features are not necessarily drawn to scale.

FIG. 1A shows the excitation spectra of a number of biological molecules, and FIG. 1B, shows the emission spectra of the same biological molecules. Proteins can serve as endogenous fluorophores and can be detected or tracked by monitoring the protein's fluorescence emission. FIG. 1C shows an image of fluorescence of tissue in the presence of paraffin using a 365 nm excitation source with an emission filter centered at 560 nm (55 nm wide bandpass). FIG. 1D shows paraffin fluorescence using a 280 nm excitation source and an emission filter centered at 405 nm (20 nm wide bandpass). As shown in FIG. 1D, paraffin can undergo fluorescence without appreciable fluorescence of tissue in an embedded sample. The results indicate that contrast between tissue and paraffin may be further enhanced by examining fluorescence in the region of the paraffin.

FIGS. 2A, 2D, and 2G are images captured using a white light source with a long pass emission filter with a cut-on wavelength at 405 nm; FIGS. 2B, 2E, and 2H are images captured using a 470 nm excitation source with an emission filter centered at 545 nm (30 nm bandpass). 2C, 2F, and 2I are images captured using a 300 nm excitation source with an emission filter centered at 545 nm (30 nm bandpass). FIGS. 2A to 2C are images of the adipose tissue. FIGS. 2D to 2F are images of the uterus tissue. FIGS. 2G to 2I are images of an embedded tissue of unknown type.

FIGS. 3A and 3B show the fluorescence and H&E images of the tissue section, respectively. A pathologist annotation (blue circle) indicates a large region of interest containing a majority of carcinoma cells as compared to the surrounding tissue which contains other cell types in the autofluorescence image in FIG. 3C and the H&E in FIG. 3D.

FIGS. 5C and 5D show in gray-scale two fluorescence images captured using a 300 nm excitation source with an emission filter centered at 545 nm (30 nm wide bandpass) and the corresponding depth map of each tissue embedded in the paraffin generated based on their fluorescence images.

DETAILED DESCRIPTION

The present methods generally utilize autofluorescence of endogenous fluorophores in tissues (and cell preparations) to distinguish tissue from an embedding medium such as paraffin or an epoxy resin. The present disclosure will generally describe the present methods as applied to tissues, but it should be understood that such descriptions apply to cell preparations as well. In some embodiments, the tissue or cell preparation is selected from the group consisting of tissue, cell pellets, and cell spheroids (which may comprise two or more cell types). Contrasting between tissue and an embedding medium can be achieved by irradiating an embedded sample such as a formalin-fixed paraffin-embedded (FFPE) tissue block at an appropriate wavelength and detecting the resulting endogenous autofluorescence emission from the tissue. The autofluorescence emission can be used to identify components of the tissue and locations thereof. For example, the present methods can be used to determine a percentage of tissue located at a surface of a formalin-fixed paraffin-embedded (FFPE) tissue block. The fluorescence methods of the present disclosure can be performed prior to biological analysis or staining of a tissue section. In some embodiments, the present methods reduce or avoid staining of tissue sections. The present methods are effective for a wide variety of tissue types and can be used to identify tissue components in cases where such components are difficult to distinguish under normal lighting conditions.

Figure 1A:
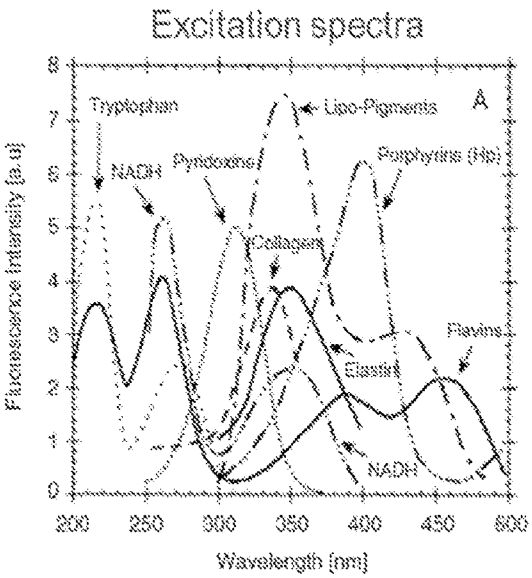
FIGS. 1A and 1B show graphs of the excitation spectra and the emission spectra of various fluorophores endogenous to human tissue.
Figure 1B:
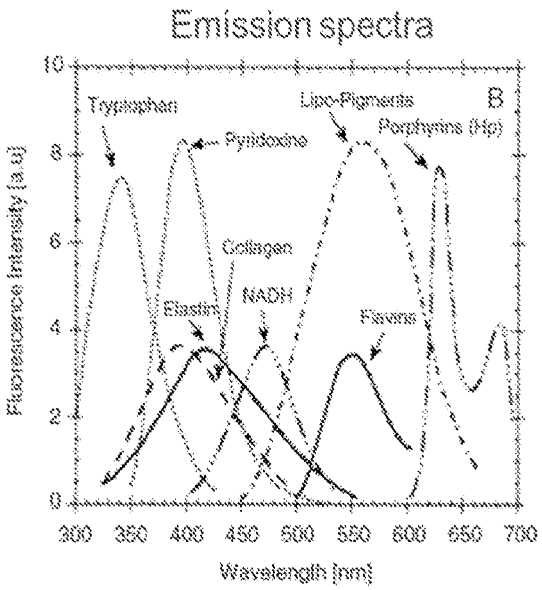

Fluorescence, which is the emission of light by a substance that has absorbed electromagnetic radiation, is commonly used to elucidate the presence or amount of an analyte. Fluorescent compounds are capable of absorbing and emitting light under certain conditions, where the emitted light is generally of lower energy. Autofluorescence is natural emission of light by biological molecules, generally at a wavelength peak or pattern, when the molecules are irradiated at certain wavelengths. Each fluorescent biological molecule has its own excitation and emission spectrum. In human and animal tissue, proteins such as collagen and elastin are capable of autofluorescence. FIG. 1A shows the excitation spectra of a number of biological molecules, and FIG. 1B shows the emission spectra of the same biological molecules. Proteins can serve as endogenous fluorophores and can be detected or tracked by monitoring the protein's autofluorescence emission.

Figure 1C:
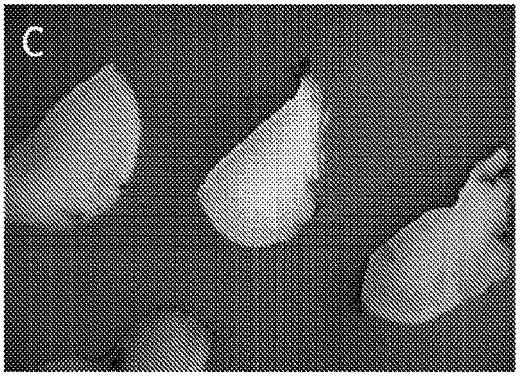
FIGS. 1C and 1D are collections of fluorescence emission images of various slices of a FFPE tissue block sample.
Figure 1D:
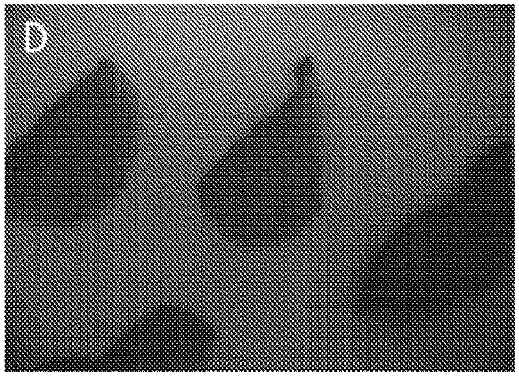

FIG. 1C shows an image of autofluorescence of tissue in the presence of paraffin using a 365 nm excitation source with an emission filter centered at 560 nm (55 nm wide bandpass). FIG. 1D shows paraffin fluorescence using a 280 nm excitation source and an emission filter centered at 405 nm (20 nm wide bandpass). As shown in FIG. 1D, paraffin can undergo fluorescence without appreciable autofluorescence of tissue in an embedded sample. The results indicate that contrast between tissue and paraffin may be further enhanced by examining fluorescence in the region of the paraffin.

Table 1 shows excitation and emission maxima of endogenous fluorophores which can be used for identifying tissue components. Table 1 is adapted from Ramanujam, N. Fluorescence Spectroscopy of Neoplastic and Non-Neoplastic Tissues. Neoplasia. 2000 2, 89-117.

TABLE 1

| Endogenous Fluorophores | Excitation Maxima (nm) | Emission Maxima (nm) |
|---|---|---|
| Amino Acids | | |
| Tryptophan | 280 | 350 |
| Tyrosine | 275 | 300 |
| Phenylalanine | 260 | 280 |
| Structural proteins | | |
| Collagen | 325, 360 | 400, 405 |
| Elastin | 290, 325 | 340, 400 |
| Enzymes and coenzymes | | |
| FAD, Flavins | 450 | 535 |
| NADH | 290, 351 | 440, 460 |
| NADPH | 336 | 464 |
| Vitamins | | |
| Vitamin A | 327 | 510 |
| Vitamin K | 335 | 480 |
| Vitamin D | 390 | 480 |
| Vitamin B6 pyridoxine | 332, 340 | 400 |
| Vitamin B6 pyridoxamine | 335 | 480 |
| Vitamin B6 pyridoxal | 330 | 385 |
| Vitamin B6 pyridoxic acid | 315 | 425 |
| Vitamin B6 pyridoxal 5'-phosphate | 330 | 400 |
| Vitamin B12 | 275 | 305 |
| Lipids | | |
| Phospholipids | 436 | 540, 560 |
| Lipofuscin | 340-395 | 540, 430-460 |
| Ceroid | 340-395 | 430-460, 540 |
| Porphyrins | 400-450 | 630, 690 |

Table 2 shows common peak excitation wavelengths identified across many tissue types. Spectral contributions from common molecular components/endogenous fluorophores are shared between tissue types. Table 2 is adapted from Favreau, P. F. et al. Label-free spectroscopic tissue characterization using fluorescence excitation-scanning spectral imaging. J. Biophotonics. 2019; e201900183.

TABLE 2

| Peak excitation wavelength (nm) | Tissues |
|---|---|
| 360 | Heart, liver, lung, pancreas, skeletal muscle, trachea |
| 375 | Colon, esophagus, kidney, spleen |
| 395 | Colon, esophagus, kidney, pancreas, trachea |
| 480 | Heart, kidney, liver, lung, skeletal muscle, spleen, trachea |

Figure 2:
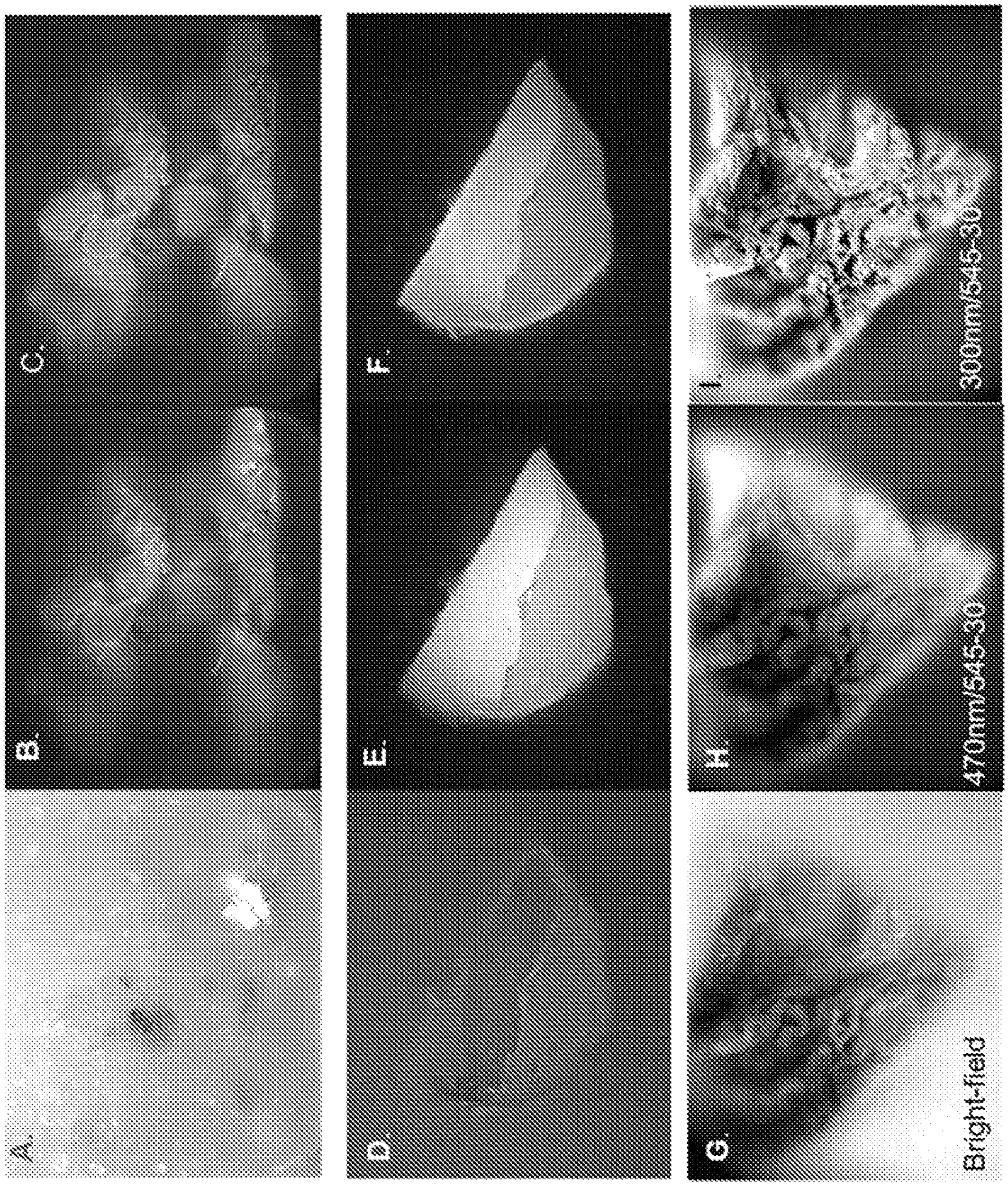
FIGS. 2A-I shows brightfield and fluorescence images of different tissue types.

FIG. 2 shows brightfield and autofluorescence images of different tissue types. The peak excitation and emission wavelengths for autofluorescence vary between tissue types due to variations in concentrations of the common molecular components or endogenous fluorophores; structural proteins, enzymes, lipids and porphyrins. Brightfield images show less subsurface topology in adipose (panel A), uterus (panel D) and colon (panel G). Autofluorescence of adipose was optimal using the 470 nm excitation filter—545 emission, 30 nm bandpass width (panel B) as compared to the 300 nm emission filter—545 emission, 30 nm bandpass width (panel C). For uterus and colon, autofluorescence peak excitation/emission was optimal using the 300 nm excitation filter with a 545 nm emission, with 30 nm bandpass width (panels F and I) as compared to the 470 nm excitation filter (panels E and H).

For determination of the optimal filter set to use for imaging autofluorescence, Tables 1 and 2 can be used as a general guide, and multiple filter sets can be tested, including filter sets that are commercially available. Adipose tissue contains a high concentration of phospholipids which have a peak excitation around 436 nm and 540 nm emission. For uterus and colon, structural proteins are predominant which have a peak excitation at 325 nm and 290 nm respectively and emission at 400 nm emission.

Fluorescence-based imaging allows for a greatly improved 2-dimensional (2D) determination of the sub-surface topology of the tissue section compared to white light imaging. This is due to the illumination of tissue autofluorescence of cellular components such as collagen and elastin using different excitation and emission filters. This adds a great deal of context to the sub-surface topology relative to white light illumination alone and leads to improved algorithm development for use in the automation of microtomy for trimming.

Prior methods for trimming using white light imaging is largely qualitative and inaccurate when used to analyze different tissue and paraffin types due to lack of sensitivity to variability of optical and surface characteristics of tissue and paraffin. The present method provides a quantitative method for determining the optimal plane of sectioning and also the estimation of how far to trim before an optimal quantity of tissue is exposed. The benefit of this method is based on the determination of the tissue sub-surface topology by autofluorescence-based imaging that is not visible with white light which will allow for highly improved algorithms for trimming in an automated microtomy setup.

Determining an Amount of Tissue or Cell Preparation Exposed at a Surface

The present disclosure provides a method of determining an amount of tissue or cell preparation exposed at a surface of a sample embedded in an embedding medium.

In manual sectioning, a technician's qualitative assessment of exposed tissue can be wasteful in the use of the tissue sample, as they might trim too far. In some embodiments, the present methods use an algorithm based on autofluorescence of the tissue sample and a local focus measurements to estimate the topology of tissue surface buried in the paraffin and to identify plane of sectioning to increase or maximize tissue use. By quantitatively assessing the area of tissue exposed, the usage of the tissue can be increased to achieve its diagnostic potential. The present method can also speed up the trimming process by estimating how far to trim before the appropriate percentage of tissue is exposed, and it can do so in a highly accurate way that is quantitative as opposed to the qualitative method employed using a white light illuminated image and the human eye or algorithms associated with white light illumination.

The present method comprises irradiating the embedded tissue or cell preparation sample at a wavelength which causes endogenous components of the tissue to autofluoresce; obtaining an image of the autofluorescence emitted by the embedded tissue or cell preparation sample; and determining a percentage of the image at the surface of the embedding medium which is occupied by tissue or cell preparation.

In some embodiments, the percentage of the image at the surface of the embedding medium which is occupied by tissue is determined by: slicing a tissue section from the embedded tissue sample, wherein the embedded tissue sample comprises the tissue and the embedding medium; irradiating the embedded tissue sample with electromagnetic radiation having an excitation wavelength; generating a fluorescence image from an autofluorescence emission of the embedded sample; determining a local focus measure for pixels of the fluorescence image; constructing a depth map of the tissue based on evaluating image blur of the autofluorescence; and determining a sectioning plane for the embedded sample, based on the depth map.

The present disclosure deploys focus-measure-based detection methods to quantitate the amount of exposed tissue in the FFPE block during trimming. The autofluorescence imaging provides additional information that potentially provides more consistent signals across various tissue types. The autofluorescence imaging will be used to quantitate the amount of tissue that is exposed for optimal trimming and sectioning.

In some embodiments, the local focus measure is determined by applying an operator to the fluorescence image. For example, the operator can be a modified Laplacian operator. In some embodiments, the local focus measure is measured in an n-by-n neighborhood surrounding a plurality of pixels in an input image.

In some embodiments, the method further comprises performing one or more processing operations to obtain the fluorescence image. The processing operations can be selected from the group consisting of image registration, contrast enhancement, and image smoothing.

In some embodiments, the desired amount of tissue within the sectioning plane and a cut tissue section is from 10 to 100%. For example, in some embodiments, the desired amount of tissue within the sectioning plane and a cut tissue section is about 10%, about 20%, about 30%, about 40%, about 50%, about 60%, about 70%, about 80%, about 90%, or about 100% or within a range with endpoints between any two of the foregoing values. In some embodiments, the exposed tissue is identified by normalizing a focus metric on each slice image on a first slice image. In some embodiments, the tissue section from the embedded tissue sample will be cut at the sectioning plane when the desired amount of tissue is present. In some embodiments, after the desired amount of tissue is determined, the tissue section from the embedded sample of the sectioning plane is cut.

Identifying Different Cell Types in an Embedded Tissue Sample

The present disclosure also provides a method of identifying different cell types in an embedded tissue sample. The method comprises irradiating the embedded tissue sample at a wavelength which causes endogenous components of a tissue to autofluoresce; obtaining an image of the autofluorescence emitted by the tissue sample; and identifying different cell types in the image of the autofluorescence emitted by the tissue sample based upon autofluorescence characteristics.

In some embodiments, the different cell types in the embedded tissue sample are determined by: exposing a tissue section from the embedded tissue sample, wherein the embedded tissue sample comprises a tissue and an embedding medium; irradiating the embedded tissue sample with electromagnetic radiation having an excitation wavelength; generating a fluorescence image from autofluorescence emission of the embedded sample; determining a local focus measure for pixels of the fluorescence image; and constructing a depth map of the tissue based on evaluating image blur of the fluorescence. In some embodiments, the depth map of the tissue is a subsurface topology of the tissue within the embedding medium.

In some embodiments, the fluorescence images are captured by an imaging device.

In some embodiments, the local focus measure is determined by applying an operator to the fluorescence image, such as a modified Laplacian operator. In some embodiments, the local focus measure is measured in an n-by-n neighborhood surrounding a plurality of pixels in an input image. In some embodiments, the method further comprises performing one or more processing operations to obtain the fluorescence image, such as processing operations selected from the group consisting of image registration, contrast enhancement, and image smoothing.

In some embodiments, a predicted optimal plane of sectioning for the tissue sample is based on evaluating the subsurface topology of the tissue within the embedding medium.

Training an Artificial Intelligence (AI) System to Identify a Region of Interest (ROI) in an Embedded Tissue Sample The present disclosure also provides a method of training an artificial intelligence (AI) system to identify a region of interest (ROI) in an embedded tissue sample comprising a tissue and an embedding medium. The method comprises irradiating the embedded tissue sample at a wavelength which causes endogenous components of the tissue to autofluoresce; obtaining an image of the autofluorescence emitted by the embedded tissue sample; annotating the image to indicate the ROIs in the image; and inputting the annotated image into the AI system, wherein the AI system learns to identify ROIs in unannotated images.

In some embodiments, the embedded tissue sample has been stained with a hematoxylin and eosin (H&E) stain, an immunohistochemistry (IHC) stain, or an immunofluorescence (IF) stain for protein markers. In some embodiments, the image of the embedded tissue sample is annotated on a whole slide image of the embedded tissue sample.

In some embodiments, the embedded sample is irradiated as part of a tissue block, and the method further comprises slicing the embedded sample from the tissue block as a tissue section.

In some embodiments, the trained AI system is adapted for identifying a ROI containing tumor cells in accordance with tumor enrichment methods for molecular assays.

In some embodiments, the AI system comprises at least one of a machine learning system, a deep learning system, a neural network, a convolutional neural network, a fully convolutional neural network, a segmentation convolutional neural network, a recurrent neural network, a statistical model-based system, or a deterministic algorithm-based analysis system.

In some embodiments, the AI system learns to identify ROIs in unannotated images by: obtaining an untrained or pretrained AI system; staining the embedded tissue sample with a stain detectable by bright field or autofluorescence-based imaging; generating one or more stained images of a stained embedded tissue sample by bright field or autofluorescence imaging; annotating the ROI of the stained embedded tissue sample on the one or more stained images; mapping the annotated ROI of the one or more stained images to the unstained autofluorescence image; and training the untrained AI system by using a mapped fluorescence image. In some embodiments, AI system training data is obtained from the mapped autofluorescence image in order to train the untrained or pretrained AI system.

In some embodiments, the AI system is adapted for identifying the ROI on an unstained embedded tissue sample. In some embodiments, the ROI identifies tumor containing regions. In some embodiments, the ROI is identified by detecting an autofluorescence level corresponding to concentration of endogenous fluorophores from extracellular matrix and cytoplasm surrounding tumor nuclei.

In some embodiments, the autofluorescence level of the extracellular matrix and cytoplasm surrounding the tumor nucleus is compared to a autofluorescence level of a control sample. The control sample can comprise a control nucleus, control cytoplasm, control stroma, or control extracellular matrix components. In some embodiments, the autofluorescence level of the extracellular matrix or cytoplasm surrounding the tumor nucleus is lower than the autofluorescence level of the control sample. The control nucleus may be smaller than tumor nuclei with fine chromatin and a single nucleolus.

In some embodiments, the method further comprises: mounting the embedded sample as a tissue section onto a slide and imaging the tissues using a first filter and a second filter; treating the tissue section to remove the embedding medium and to permeabilize nuclei to facilitate a stain for nuclei; applying a stain such as DAPI which is specific for nuclei to the tissue section to form a nuclei-stained tissue section; imaging the nuclei-stained tissue section to produce a nuclei-stained tissue section image; removing the nuclei stain mounting medium; applying a hematoxylin and eosin (H&E) stain, an immunohistochemistry (IHC) stain, or an immunofluorescence (IF) stain to produce a cell-stained tissue section; coverslipping the cell-stained tissue section; and imaging the cell-stained tissue section using bright field imaging to produce the stained image.

The present disclosure provides a workflow where the unstained deparaffinized tissue is first imaged for autofluorescence in the FITC and DAPI filters to identify cytosol and extracellular matrix. The deparaffinized tissue is then treated by either pepsin or e-field treatment to allow DAPI staining to penetrate the nuclei. The DAPI stained tissue is then imaged again for fluorescence in the FITC and DAPI channels. The first image shows FITC autofluorescence only. The second image shows FITC and DAPI stained fluorescence which very clearly distinguishes the cytosol and extracellular matrix from the nuclei. An added benefit of this technique is that the nuclear boundaries are very clearly identified even between crowded nuclei. Hence, for AI training, the second DAPI stained image could be used as a base and mapped back to H&E images to accomplish nuclear segmentation of tumor nuclei versus surrounding normal cells and extracellular matrix. This workflow would save the pathologist from the painstaking process of annotating H&E stained section for the nuclei segmentation model training.

The workflow will assist in the training of machine learning algorithms developed for macrodissection as well as for nuclear segmentation in a more clear and concise manner than using data derived by pathologists and computational biologists analysis of H&E stained tissue sections.

The present disclosure describes a workflow that may be used for (1) algorithm-based detection methods to perform nuclear segmentation for nuclear morphometric analysis, and (2) algorithm-based detection methods to perform macrodissection of tumor regions of interest for subsequent genomic testing methods. The algorithms developed using this workflow may be deployed using an unstained FFPE block during microtomy or using a tissue section on a slide.

Prior techniques for nuclear segmentation algorithm development requires a large database of painstakingly annotated H&E images. The present methods do not require pathologist annotation as the DAPI stained nuclei are very clearly distinguished from the autofluorescence seen in the cytosolic compartments and extracellular matrix.

Prior techniques for algorithm development for macrodissection also required pathologist annotation of H&E stained tissue sections that are then mapped back to the autofluorescence image of the block face or a tissue section mounted onto a slide. Algorithms developed for macrodissection may use differences in the size of tumor and normal nuclei, and they can quantitate the number of tumor cells in a region of interest for selection.

Preparing a Tissue Specimen Comprising a Region of Interest (ROI) from an Embedded Sample The present disclosure also provides a method of preparing a tissue specimen comprising a region of interest (ROI) from an embedded sample, comprising: obtaining a trained AI system adapted for identifying the ROI from an unstained embedded sample; irradiating the embedded sample comprising a tissue and an embedding medium with electromagnetic radiation having an excitation wavelength; generating a fluorescence image of the embedded sample; using the trained AI system to identify the ROI in the embedded sample based on the fluorescence image and without staining the embedded sample; and collecting a portion of the embedded sample identified as having the ROI as the tissue specimen. The fluorescence image can be generated from a tissue section comprising the embedded sample and/or from a tissue block comprising the embedded sample. In some embodiments, the fluorescence image is generated from a tissue section, and a collected portion of the embedded sample is collected from a tissue block.

In some embodiments, the embedding medium is removed from the collected portion of the embedded sample to provide the tissue specimen. In some embodiments, cellular components are removed from the tissue specimen to provide a nucleic acid specimen and determining a nucleic acid sequence from the nucleic acid specimen.

In some embodiments, the trained AI system is obtained by: irradiating the embedded tissue sample at a wavelength which causes endogenous components of the tissue to autofluoresce; obtaining an image of the autofluorescence emitted by the embedded tissue sample; annotating the image to indicate the ROIs in the image; and inputting the annotated image into the AI system, wherein the AI system learns to identify ROIs in unannotated images.

In some embodiments, the AI system comprises at least one of a machine learning system, a deep learning system, a neural network, a convolutional neural network, a fully convolutional neural network, a segmentation convolutional neural network, a recurrent neural network, a statistical model-based system, or a deterministic algorithm-based analysis system.

In some embodiments, the trained AI system is obtained by: imaging the embedded sample as part of the tissue block using autofluorescence and slicing the embedded sample from the tissue block as the tissue section; mounting the embedded sample as the tissue section onto a slide and imaging the tissues using a first filter and a second filter; treating the tissue section to remove the embedding medium and to permeabilize nuclei to a stain for nuclei; applying a nuclei stain in a nuclei stain mounting medium to the tissue section to form a nuclei-stained tissue section; imaging the nuclei-stained tissue section to produce a nuclei-stained tissue section image; removing the nuclei stain mounting medium; applying a hematoxylin and eosin (H&E) stain, an immunohistochemistry (IHC) stain, or an immunofluorescence (IF) stain to produce a cell-stained tissue section; coverslipping the cell-stained tissue section; and imaging the cell-stained tissue section using bright field imaging to produce the stained image.

Imaging a Sample of a Biological Tissue

The present disclosure also provides a method of imaging a sample of a biological tissue comprising: irradiating a biological tissue sample at an excitation wavelength which causes endogenous components of the biological tissue to autofluoresce; obtaining an image of the autofluorescence emitted by the biological tissue sample to identify regions of the biological tissue comprising extracellular matrix; and staining nuclei in the biological tissue sample with a nuclear stain to identify regions of the biological tissue comprising cellular nuclei.

In some embodiments, the biological tissue sample is deparaffinized and pretreated with a cleaning solution. For example, the cleaning solution can comprise xylene and pepsin digestion or e-field treatment with rehydration. In some embodiments, the nuclear stain contains fluorescent mounting media. In some embodiments, the biological tissue sample is scanned by fluorescence imaging. In some embodiments, the DAPI is removed by soaking the tissue section in water.

In some embodiments, a trained AI system is developed.

In some embodiments, the step of identifying regions of the biological tissue comprising cellular nuclei allows for identification of tumor cells and nuclear stained tumor cells.

In some embodiments, the biological tissue sample is used to develop each autofluorescence image. In some embodiments, the autofluorescence image is a first image. In some embodiments, a second image is obtained by staining the nuclei in the biological tissue sample with a nuclear stain. In some embodiments, the first image and the second image identify tumor boundaries in the biological tissues. In some embodiments, the second image is mapped to an H&E or IHC image in order to show nuclear segmentation of tumor cells.

In some embodiments, the regions of the biological tissue comprising cellular nuclei are tumor nuclei. In some embodiments, the regions of the biological tissue comprising cellular nuclei are identified by detecting the autofluorescence level of the extracellular matrix surrounding the tumor nuclei. The autofluorescence level of the extracellular matrix surrounding the tumor nuclei can be compared to a autofluorescence level of a control sample. The control sample can comprise control nuclei, control cytoplasm, control stroma, or control extracellular matrix components. The autofluorescence level of the extracellular matrix surrounding the tumor nuclei may be lower than the autofluorescence level of the control sample. In some embodiments, the control nuclei are smaller than the tumor nuclei are mono-nucleate, contains one nucleoli and fine chromatin.

Additional Information Regarding the Present Methods

Various embodiments of the foregoing methods may be implemented in any desirable manner. In some embodiments, the embedding medium is paraffin. In some embodiments, the embedding medium is an epoxy resin.

In some embodiments, the autofluorescence emission is detected using an imaging device. In some embodiments, the imaging device comprises a camera such as a digital camera. In such cases, an embedded sample comprising tissue and an embedding medium such as paraffin is irradiated with light and the resulting autofluorescence emission is captured using a digital camera. The presence of autofluorescence in the digital image provides an indication that tissue is present in the sample under study. In some embodiments, the present method is performed using an optical system comprising a digital camera and a microtome. In some embodiments, the present method is performed using a fluorescence microscope.

In some embodiments, the embedding medium exhibits no substantial autofluorescence when irradiated at a chosen wavelength.

The present methods may be used to analyze a tissue of any type. In some embodiments, the tissue is a human tissue. In some embodiments, the tissue is an animal tissue. In some embodiments, the tissue is a mouse, rat, dog, or primate tissue. The present method may be used to analyze a tissue section from any organ or anatomical part. In some embodiments, the tissue is isolated from the breast, prostate, lung, colon, rectum, urinary bladder, uterine corpus, thyroid, kidney, oral cavity (e.g., tonsil), pancreas, liver, cervix, stomach, small intestine, brain, spinal cord, heart, bone, joints, esophagus, gallbladder, adipose, skin, spleen, placenta, penis, urethra, fallopian tube, ovary, vulva, adrenal glands, appendix, or eye. In some embodiments, the tissue is pelleted cells from a human or an animal source. In some embodiments, the present method is used to test a diseased or healthy tissue. In some embodiments, the present method is used to identify cancer, infectious disease, metabolic disease, degenerative disease, inflammatory disease, or a combination thereof.

In some embodiments, the embedded sample is a formalin-fixed paraffin-embedded sample. The formalin-fixed paraffin-embedded sample may be formed from any type of paraffin. In some embodiments, the paraffin is a blend of fully refined paraffin wax and a synthetic resin or polymer. In some embodiments, the paraffin comprises dimethyl sulfoxide (DMSO). In some embodiments, the formalin-fixed paraffin-embedded sample is formed from granulated paraffin wax, fully refined paraffin wax, semi-refined paraffin wax, or a combination thereof. Thus, in some embodiments, a tissue may be distinguished from granulated paraffin wax, fully refined paraffin wax, or semi-refined paraffin wax in a formalin-fixed paraffin-embedded sample. In some embodiments, the formalin-fixed paraffin-embedded sample is formed from Spectrum paraffin, Millipore paraffin, Fisherfinest Histopath paraffin wax, EMS Paramat, Paraplast, Polyfin, Sakura Finetek Tissue Tek VIP, Leica Surgipath Paraplast, or a combination thereof.

In some embodiments, the embedding medium is an epoxy resin. In some embodiments, the epoxy resin is a glycidyl epoxy resin. In some embodiments, the epoxy resin is a non-glycidyl epoxy resin. In some embodiments, the epoxy resin is a non-glycidyl resin selected from an aliphatic and cyclo-aliphatic resin. In some embodiments, the epoxy resin is a glycidyl epoxy selected from glycidyl amine, glycidyl ester, glycidyl ether, and a combination thereof. In some embodiments, the epoxy resin is ethylene glycol diglycidyl ether. In some embodiments, the epoxy resin is Araldite, Quetol, Epon 812, Embed 812, Poly-Bed 812, or a combination thereof. In some embodiments, the epoxy resin is a glycerol-based aliphatic epoxy resin. In some embodiments, embedding a tissue in an epoxy resin provides tissue sections having improved morphology.

In some embodiments, the embedded sample is cut or sliced to provide a slice and a trimmed block. In some embodiments, the embedded sample is sliced or trimmed on a microtome. In some embodiments, the autofluorescence of an embedded sample is detected while the embedded sample is being sliced or trimmed by a microtome. The trimmed block is irradiated with light, and analyzed to determine the presence of autofluorescence. Imaging may be used to determine the presence of autofluorescence. The trimming and/or irradiation process is repeated as needed. For example, the trimming/irradiation process may be repeated until the surface of the tissue is found.

In some embodiments, autofluorescence of one or more endogenous species is measured quantitatively to determine the location of tissue in an embedded sample.

In some embodiments, pixel intensity of a fluorescence digital image is used to determine the components and/or location of a tissue in an embedded sample. A trimmed block is irradiated with light, and a digital image is acquired using a fluorescence microscope. The fluorescence microscope system comprises software that converts photons detected during fluorescence analysis to pixel intensity values, allowing the user to determine the pixel intensity for a region of interest. The trimmed block may be further sliced or trimmed and analyzed by the fluorescence microscope system to provide a second digital image. A comparison of the pixel intensity of two or more digital images can be used to determine the location of the tissue in the embedded sample. For example, an increase in pixel intensity values between two digital images can indicate that the tissue in the trimmed block is exposed and is ready to be cut and used for biological testing.

In some embodiments, the present method is used to determine the components and/or location of a surface of a tissue sample in an embedded sample. In some embodiments, the present method is used to determine the location of a tissue-to-embedding medium transition or embedding medium-to-tissue transition in an embedded sample. In some embodiments, the present method is used to locate a tissue in its entirety.

In some embodiments, the method comprises slicing a section from the embedded sample and accepting or rejecting the section based on the determined location of the tissue surface. In some embodiments, the irradiating is performed multiple times and the embedded sample is cut prior to each irradiation.

The autofluorescence emission of an endogenous species in tissue may be used to determine the components and/or location of a tissue in an embedded sample. Any endogenous fluorophore in tissue may be used. In some embodiments, the endogenous fluorophore is collagen, elastin, tryptophan, a porphyrin, a flavin, NADH, pyridoxin, a lipo-pigment, or a combination thereof. In some embodiments, the autofluorescence emission of collagen is used to determine the location of a tissue in an embedded sample. In some embodiments, the autofluorescence emission of elastin is used to determine the location of a tissue in an embedded sample. In some embodiments, the autofluorescence emission of tryptophan is used to determine the components and/or location of a tissue in an embedded sample. In some embodiments, one or more of collagen, elastin, and tryptophan are used to determine the location of a tissue in an embedded sample.

In some embodiments, an excitation light having a wavelength of from about 320 nm to about 380 nm is used to detect collagen autofluorescence. In some embodiments, collagen maximum autofluorescence emission is detected at a wavelength of from about 375 nm to about 425 nm.

In some embodiments, an excitation light having a wavelength of from about 320 nm to about 380 nm is used to detect elastin autofluorescence. In some embodiments, elastin maximum autofluorescence emission is detected at a wavelength of from about 400 nm to about 450 nm.

In some embodiments, an excitation light having a wavelength of from about 180 nm to about 230 nm is used to detect tryptophan autofluorescence. In some embodiments, tryptophan maximum autofluorescence emission is detected at a wavelength of from about 300 nm to about 350 nm.

The embedded sample may be irradiated with light having any suitable wavelength. In some embodiments, an embedded sample is irradiated with light having a wavelength of from about 200 nm to about 600 nm. Thus, in some embodiments, an embedded sample is irradiated with light having a wavelength of from about 200 nm to about 600 nm, from about 200 nm to about 550 nm, from about 200 nm to about 500 nm, from about 200 nm to about 450 nm, from about 200 nm to about 400 nm, from about 200 nm to about 350 nm, from about 250 nm to about 600 nm, from about 250 nm to about 550 nm, from about 250 nm to about 500 nm, from about 250 nm to about 450 nm, from about 250 nm to about 400 nm, from about 300 nm to about 500 nm, from about 300 nm to about 550 nm, from about 300 nm to about 600 nm, from about 350 nm to about 600 nm, from about 400 nm to about 600 nm, from about 450 nm to about 600 nm, from about 350 nm to about 550 nm, from about 350 nm to about 500 nm, from about 400 nm to about 600 nm, from about 400 nm to about 550 nm, or from about 450 nm to about 600 nm.

The autofluorescence emission of the embedded sample can be detected at any suitable wavelength, usually the maximum emission wavelengths. In some embodiments, the embedded sample has a maximum autofluorescence emission at a wavelength of from about 300 nm to about 600 nm. Thus, in some embodiments, the embedded sample has a maximum autofluorescence emission at a wavelength of from about 300 nm to about 600 nm, from about 300 nm to about 550 nm, from about 300 nm to about 500 nm, from about 300 nm to about 450 nm, from about 300 nm to about 400 nm, from about 350 nm to about 600 nm, from about 350 nm to about 550 nm, from about 350 nm to about 500 nm, from about 350 nm to about 450 nm, from about 400 nm to about 600 nm, from about 450 nm to about 550 nm, or from about 500 nm to about 600 nm.

Fluorescence methods are generally performed using a light source and a detector configured to detect fluorescence as known in the art. In some embodiments, fluorescence techniques are carried out using a light source capable of shining light at a particular wavelength or range thereof. In some embodiments, an embedded sample is irradiated using one or more light sources. In some embodiments, the light source is a light-emitting diode (LED) light source. In some embodiments, the light source is a mercury arc lamp. In some embodiments, the light source is a xenon arc lamp. In some embodiments, the light source is a LASER. In some embodiments, the present method is performed using a fluorescence system having one or more excitation filters. In some embodiments, the fluorescence system comprises an aperture and one or more emission filters. In some embodiments, the fluorescence system comprises an imaging lens and an imaging camera.

An embedded sample may be formed using any suitable method. In some embodiments, a tissue is obtained from a subject and sectioned. The tissue is contacted with a formalin solution and fixed for at least 48 hours at room temperature. The tissue is commonly dehydrated using a series of ethanol baths and then embedded into a wax block. The wax generally comprises a mixture of straight chain alkanes having a chain length of from about 20 to about 40 carbons. In some embodiments, glutaraldehyde is used as a fixative to embed a tissue in an epoxy resin. The embedded sample may be sliced or sectioned for any subsequent analysis (e.g., microscopic slide analysis).

In some embodiments, the embedded sample may be further trimmed or sectioned to form a tissue section or slice. The embedded sample may be trimmed or sectioned using any suitable method (e.g., using a microtome blade). In some embodiments, a clearing agent such as a xylene can be used to remove the embedding medium from the section. In some embodiments, the tissue section is stained using at least one stain such as a Haematoxylin and/or Eosin, Acid/Basic Fuchsin, or Gram stain. In some embodiments, the tissue section may be mounted onto a slide for analysis. The stained tissue section may undergo further analysis using any suitable method (e.g., pathological analysis using a microscope).

In some embodiments, the present methods are performed to locate an embedded tissue for use in a fluorescence in situ hybridization (FISH) testing method. In some embodiments, the present methods are performed to locate an embedded tissue for use in a chromogenic in situ hybridization (CISH) testing method.

In another embodiment, the present disclosure provides a method of determining the location of a tissue in an embedded sample by irradiating an embedded sample comprising a tissue and an embedding medium with at least one light source to produce a first fluorescence emission and a second fluorescence emission; detecting the first fluorescence emission and the second fluorescence emission; and determining the location of at least a portion of the tissue in the embedded sample based on the first fluorescence emission and the second fluorescence emission.

In some embodiments, an embedded sample is irradiated with light having a wavelength of from about 250 nm to about 325 nm. In some embodiments, an embedded sample is irradiated with light having a wavelength of from about 300 nm to about 400 nm. In some embodiments, an embedded sample is irradiated concurrently at both wavelengths. In some embodiments, bright field microscopy is used in combination with the present method to determine the location of the tissue in the embedded sample.

In some embodiments, a first fluorescence emission is generated by fluorescence of an embedding medium in the embedded sample (e.g., paraffin). In some embodiments, a second fluorescence emission is generated by autofluorescence of a tissue component present in the embedded sample. In some embodiments, the first fluorescence emission has maximum fluorescence at a wavelength of from about 375 nm to about 425 nm and the second fluorescence emission has maximum fluorescence at a wavelength of from about 500 nm to about 600 nm.

In some embodiments, the embedded sample is irradiated using two or more light sources (e.g., two, three, four, five, or six). In some embodiments, the two or more light sources are the same. In some embodiments, the two or more light sources are different. In some embodiments, the sample is irradiated simultaneously or separately by the two or more light sources.

In some embodiments, the method is performed in the absence of a dichroic filter.

In some embodiments, the method comprises front illuminating an embedded sample traversely, such as at an oblique angle of from about 10 degrees to about 20 degrees from a plane of a face of the embedded sample. In some embodiments, a fluorescence emission is collected by a lens having a high numerical aperture. In some embodiments, illumination from two or more traverse directions (e.g., left or right or top or bottom) produces a uniform excitation and emission pattern.

In some embodiments, a high numerical aperture objective lens is used for excitation and collection of emitted light, as well as a filter cube with a dichroic beam splitter with excitation and emission filters. In some embodiments, an additional lens is used after the dichroic filter to focus the emitted light onto an imaging sensor.

In some embodiments, the embedding medium is weakly autofluorescent. Thus, in some embodiments, a fluorescent dye can be added to the embedding medium. The fluorescent dye emits light at a different wavelength than the emission wavelength of an endogenous fluorophore in the tissue sample, thus a fluorescence emission from the fluorescent dye can be used to determine the location of tissue in an embedded sample. The fluorescent dye may be incorporated into the embedding medium prior to formation of the embedded sample.

In another embodiment, the disclosure provides an apparatus for slicing a tissue section from an embedded sample. The apparatus comprises a microtome comprising a sample holder adapted for linear motion, a knife holder and a knife held by the knife holder opposite the sample holder, such that when the sample holder is moved linearly, a sample held by the sample holder is sliced by the knife to form a tissue section; at least one light source directed at the sample holder; and an optical system positioned to capture emitted light from a sample held by the sample holder.

In some embodiments, the apparatus comprises at least two light sources. In some embodiments, the apparatus comprises at least three light sources. In some embodiments, the apparatus comprises at least four light sources.

In some embodiments, the apparatus comprises a filter cube with a dichroic beam splitter with excitation and emission filters. In some embodiments, the apparatus comprises a dichroic filter. In some embodiments, the apparatus comprises an additional lens after the dichroic filter to focus the emitted light onto an imaging sensor. In some embodiments, the apparatus comprises an emission filter in a filter cube assembly, where switching of at least one excitation source switches at least one filter.

In some embodiments, the apparatus includes one or more excitation filters. In some embodiments, the apparatus comprises an aperture. In some embodiments, the apparatus comprises a lens having a high numerical aperture. In some embodiments, the apparatus comprises one or more emission filters. In some embodiments, the apparatus comprises an imaging lens. In some embodiments, the optical system comprises a camera. In some embodiments, the optical system comprises a digital camera. In some embodiments, the optical system is capable of detecting at least one fluorescence emission.

In some embodiments, the apparatus comprises a microtome blade, at least one light source, at least one excitation filter, at least one aperture, at least one emission filter, a lens assembly, and at least one camera.

In some embodiments, the apparatus comprises a microtome blade, at least two light sources, at least two excitation filters, at least one aperture, at least two emission filters, a lens assembly, at least one camera, and at least one mechanism for switching between emission filters.

In some embodiments, the apparatus comprises a microtome blade, at least two light sources, at least two excitation filters, at least one aperture, a dual-band bandpass emission filter, a lens assembly, and at least one multi-color camera. In some embodiments, the multicolor camera has microfilters in front of each pixel.

In some embodiments, the apparatus comprises a microtome blade, at least one light source, at least one excitation filter, at least one aperture, an objective lens assembly, a tube lens or relay lens, a dichroic beamsplitter, at least one emission filter in filter cube assembly, at least one camera.

In some embodiments, switching between excitation sources is accompanied by switching filters.

The present methods and apparatus can be used with a variety of fluorescence-based imaging systems. In some embodiments, the present apparatus comprises a microtome blade, one or more light sources, one or more excitation filters, a 2-dimensional aperture, one or more emission filters, an imaging lens, and/or an imaging camera. A single-color fluorescence imaging system can be used to image an embedded sample, which typically comprises a an LED light source, an excitation filter, an aperture, an emission filter with a mechanism for switching emission filters, a lens assembly, and a camera. A multi-color fluorescence imaging system can be used to image an embedded sample, which typically comprises multiple LED light sources, excitation filters, apertures, an emission filter with a motorized wheel assembly, a lens assembly, and a camera. Other components of the fluorescence imaging systems can include two-color band-pass emission filters, a color camera having a multi-color image sensor, an objective lens assembly, a dichroic beam splitter, a tube lens or relay lens. In some embodiments, switching of the excitation source is accompanied by switching the filters in accordance with an embodiment of the disclosure.

In some embodiments, the optical system comprises a processor in communication with the optical system and configured to provide a signal based on a fluorescence emission from the sample.

EXAMPLE 1

Figure 3A:
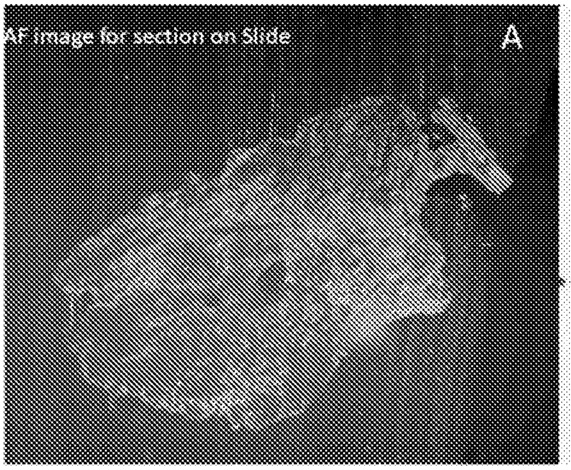
FIGS. 3A to 3D show autofluorescence images and corresponding ME brightfield images of a 5-micrometer tissue section containing breast carcinoma The autofluorescence image was captured using a 300 urn excitation coupled with a 545-30 band-pass emission filter and a camera.
Figure 3B:
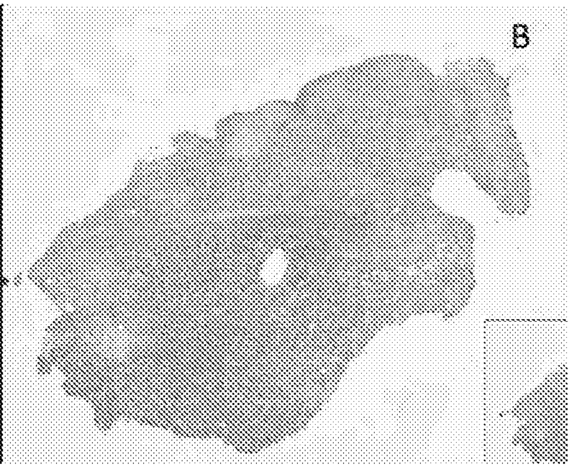
Figure 3C:
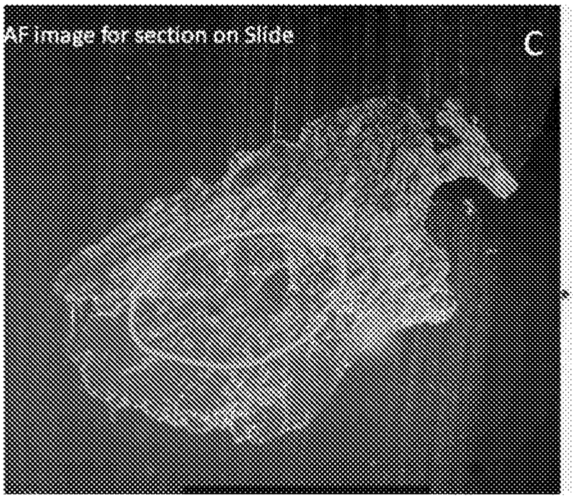
Figure 3D:
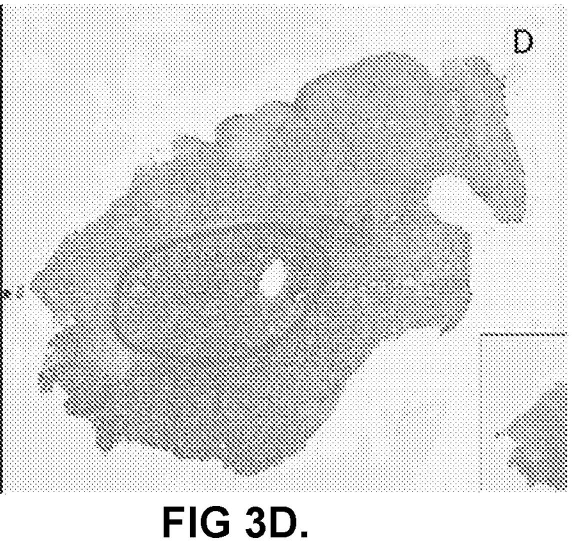

This Example illustrates an embodiment of a method for macrodissection of tumor tissue using fluorescence-based imaging of a tissue section FIGS. 3A to 3D show autofluorescence images of a 5 micrometer tissue section containing breast carcinoma and the corresponding H&E images which have been marked to indicate where a region of interest of tumor is located in relation to surrounding normal cells. An FFPE tissue section mounted onto a slide was imaged using autofluorescence in FIGS. 3A and 3C. The 5 micrometer section was then mounted onto a slide and stained by H&E, and the stained tissue sections are shown in FIGS. 3B and 3D. A pathologist annotation (blue circle) indicates a large region of interest containing a majority of carcinoma cells as compared to the surrounding tissue which contains other cell types in the autofluorescence image (FIG. 3C) and in the H&E stained section (FIG. 3D).

In tumor containing tissue, the nuclei of tumor cells are typically enlarged and nuclear material is condensed. Thus, nuclei of tumor cells do not fluoresce to the same degree as other cellular components; stroma and extracellular matrix components.

For algorithm development, a segmentation convolutional neural network (CNN) model is developed to detect tumor enriched regions of interest (ROI) generated from labeled autofluorescence images of the tissue section on the slide. To collect the labeled training data, the low resolution autofluorescence images of the sections are taken of the slide by using autofluorescence at 300 nm excitation coupled with a 545-30 band-pass emission filter. The sections are then H&E stained, and imaged at 40× magnification. A pathologist then annotates the ROI of tumor cells in the H&E stained whole slide image (WSI) and identify ROI contain 20% or greater tumor content as ground truth. By mapping this annotated ROI to the corresponding autofluorescence image, the same region is masked in the autofluorescence image as labeled training data. The segmentation CNN model trained based on this training set can be applied to autofluorescence images of unknown samples to identify tumor enriched ROI and thus enriched for genomics tests. The ROI is marked on the back of the slide for the mounted FFPE tissue section and ready for the next step in the workflow.

EXAMPLE 2

Figure 4A:
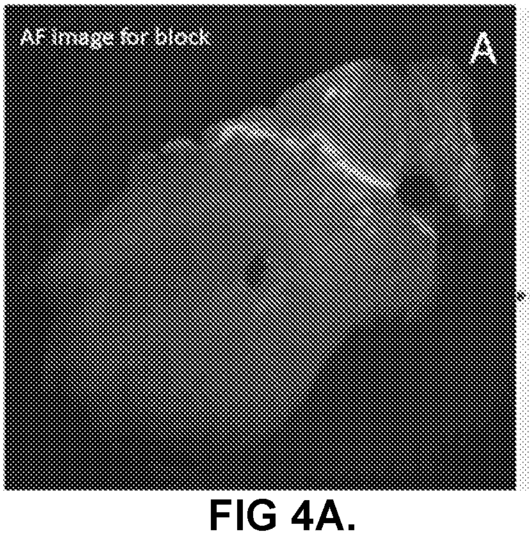
FIGS. 4A to 4D show autofluorescence images and corresponding H&E images of a tissue block containing breast carcinoma. An FFPE block on a microtome was imaged in FIG. 4A prior to microtomy of a 5-micrometer tissue section. The autofluorescence image was captured using a 300 nm excitation coupled with a 545-30 band-pass emission filter and a camera. This tissue section was H&E stained and a brightfield WSI was captured in FIG. 4B (also seen in FIGS. 3B and 3D). A pathologist annotation (blue circle) indicates a large region of interest containing a majority of carcinoma, cells as compared to the surrounding tissue which contains other cell types in the autofluorescence image in FIG. 4C and the H&E in FIG. 4D.
Figure 4B:
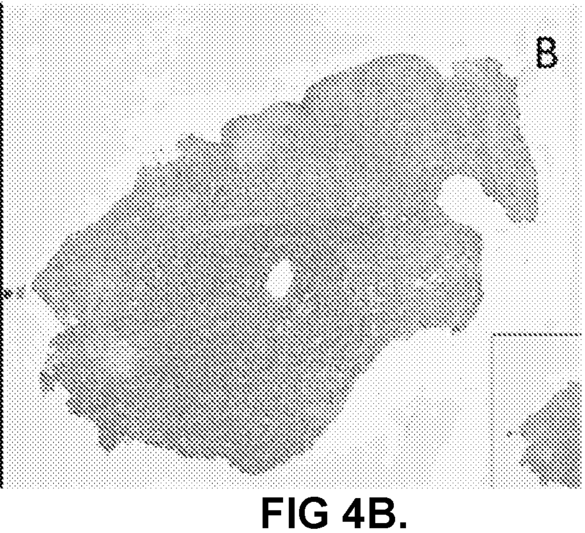
Figure 4C:
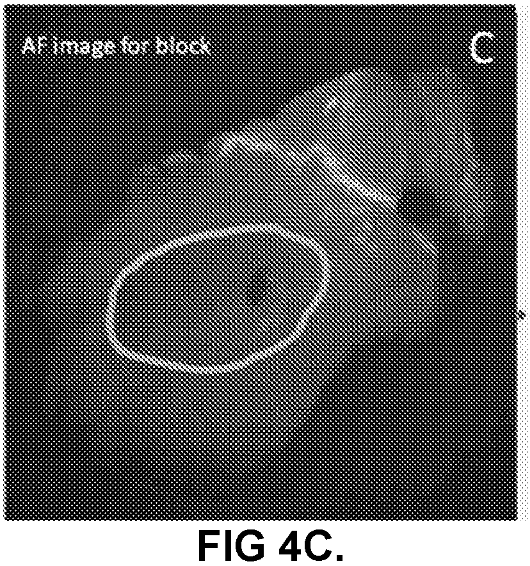
Figure 4D:
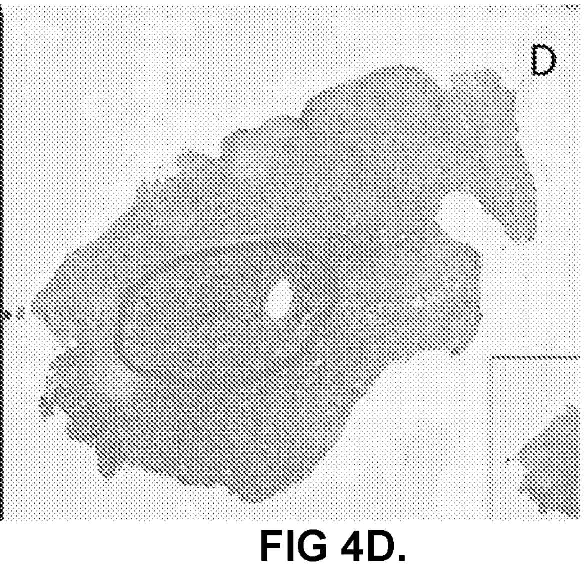

This Example illustrates an embodiment of a method for macrodissection of tumor tissue using fluorescence-based imaging of a tissue block FIGS. 4A to 4D show the autofluorescence images of a block containing breast carcinoma and the corresponding H&E images where a region of interest of tumor is located in relation to surrounding normal cells. An FFPE block containing breast carcinoma was imaged using autofluorescence in FIGS. 4A and 4C. The 5 micrometer section cut from the FFPE block was then mounted onto a slide and stained by H&E (FIG. 4B and FIG. 4D). A pathologist annotation (blue circle) indicates a large region of interest containing a majority of carcinoma cells as compared to the surrounding tissue which contains other cell types in the autofluorescence image (FIG. 4C) and in the H&E stained section (FIG. 4D).

As noted above, in tumor containing tissue, the nuclei of tumor cells are typically enlarged and nuclear material is condensed. Thus, nuclei of tumor cells do not fluoresce to the same degree as other cellular components; stroma and extracellular matrix components.

For algorithm development, a segmentation convolutional neural network (CNN) model is developed to detect tumor enriched regions of interest (ROI) generated from labeled autofluorescence images. To collect the labeled training data, the low resolution autofluorescence images of the sections are taken on the trimming stage by using autofluorescence at 300 nm excitation coupled with a 545-30 band-pass emission filter. The sections then will be mounted on the slide, H&E stained, and imaged at 40× magnification. The pathologist will then annotate the ROI of tumor cells in the H&E stained whole slide image (WSI) and identify ROI contain 20% or greater tumor content as ground truth. By mapping this annotated ROI to the corresponding autofluorescence image, the same region is masked in the autofluorescence image as labeled training data. The segmentation CNN model trained based on this training set can be applied to autofluorescence images of unknown samples to identify tumor enriched ROI and thus enriched for genomics tests. The ROI is marked on the back of the slide for the mounted FFPE tissue section and ready for the next step in the workflow.

EXAMPLE 3

This Example illustrates focus-measure-based detection methods to quantitate the amount of exposed tissue in the FFPE block during trimming. The autofluorescence imaging provides additional information that potentially provides more consistent signals across various tissue types. Algorithms will be used to quantitate the amount of tissue that is exposed for optimal trimming and sectioning. A quantitative approach to evaluate the percentage of exposed tissue in the block would enhance the expediency of the automated trimming station and conserve tissue.

In manual sectioning, the histotechnician's qualitative assessment of exposed tissue can be both wasteful use of the FFPE tissue sections as they might trim too far. By quantitatively assessing the area tissue exposed, the usage of the tissue can be optimized to achieve their diagnostic potential.

It will also speed up the trimming process by estimating how far to trim before the appropriate percentage of tissue is exposed in a highly accurate way that is quantitative as opposed to the qualitative method employed using a white light illuminated image and the human eye or algorithms associated with white light illumination.

FIGS. 5A to 5D illustrate a fluorescence based image processing system used to detect the exposed tissue. Autofluorescence imaging distinguishes tissue, which is sharply focused and subsurface tissue which appears defocused. The area of exposed tissue was estimated by measuring the local focus. A cartoon drawing of a cassette containing FFPE tissue embedded in paraffin from the top (FIG. 5A) and side (FIG. 5B) orientation shows that embedded tissue is visible at different focal planes. Fluorescence images can be used to create a depth map for the tissue block for determination of sharply versus defocused tissue.

Figure 5A:
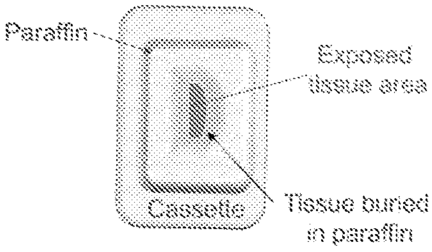
FIGS. 5A to 5D illustrate a fluorescence-based image processing system used to detect the exposed tissue. Autofluorescence imaging distinguished tissue, which is sharply focused, and subsurface tissue which appears defocused. The area of exposed tissue is estimated by measuring the local focus. A cartoon drawing of a cassette containing FFPE tissues embedded in paraffin from the top FIG. 5A and side FIG. 5B orientation shows that embedded tissue is visible at different focal planes. Fluorescence images can be used to create a depth map for the tissue block for determination of sharply versus defocused tissue.
Figure 5B:
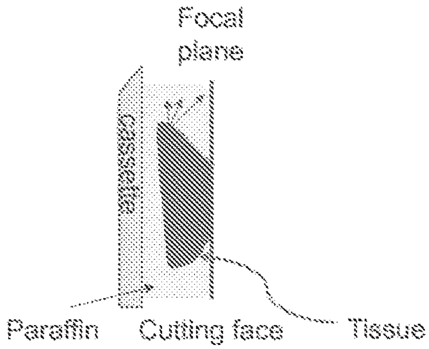
Figure 5C:
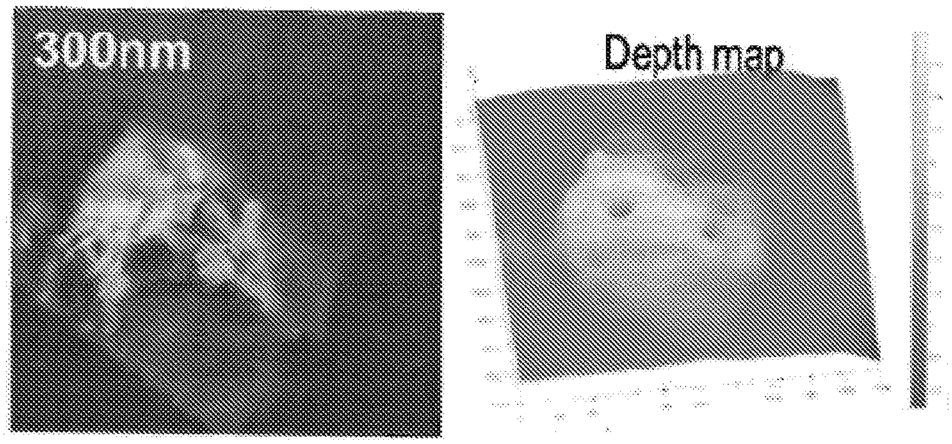
Figure 5D:
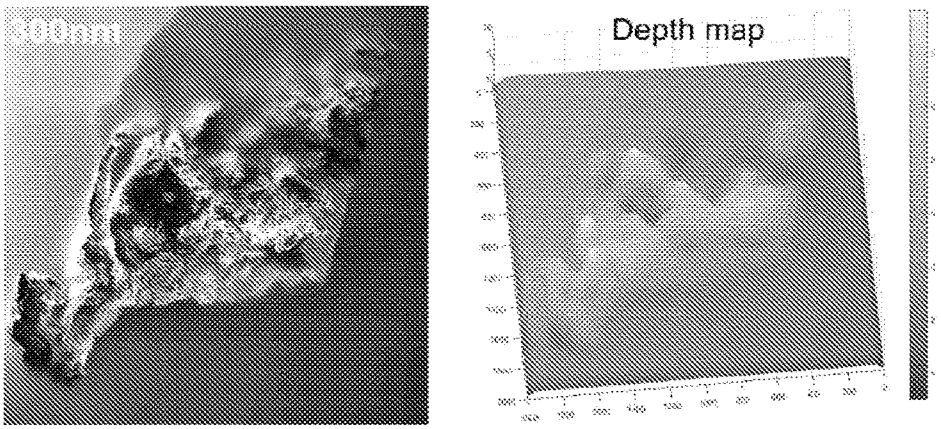

The images in FIG. 5C and FIG. 5D were collected automatically by a 6 megapixel CMOS sensor parallel to the cut surface of the tissue block after trimming each slice. To improve the image quality, several processing operations, including image registration, CLAHE contrast enhancement, and Gaussian blur, are performed. A modified Laplacian operator is applied on the whole image to determine the local focus measure for each pixel. A depth map of the tissue is constructed based on evaluating image blur. The exposed tissue surface is identified by normalizing the focus metric of each slice image on the first slice image. Tissues were sculptured into regular geometrical shapes and embedded in paraffin to serve as ground truth for evaluating the algorithm.

EXAMPLE 4

Figure 6A:
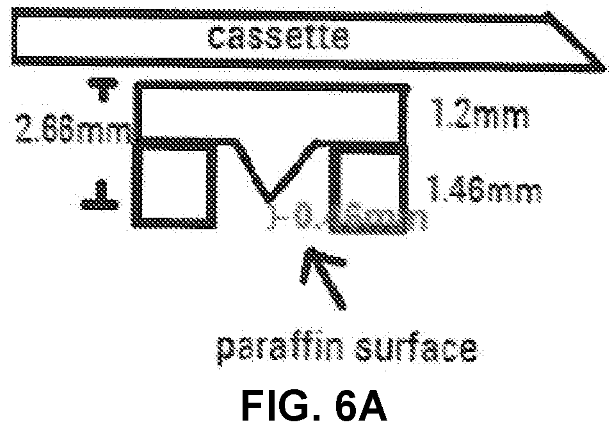
FIG. 6A is a cartoon illustration of an artificial block comprising an artificially shaped tissue for analysis by digital microscopy.
Figure 6B:
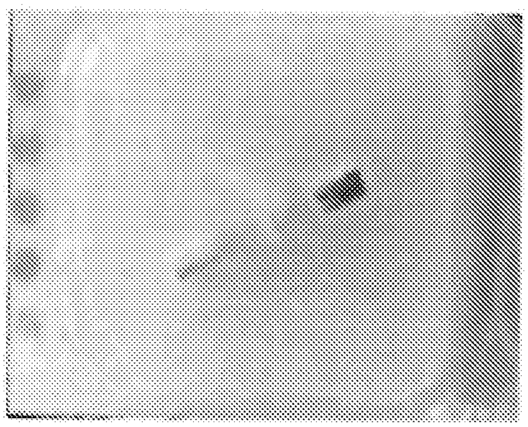
FIG. 6B is a photograph of the artificially shaped tissue embedded in paraffin to make an artificial FFPE block.
Figure 6C:
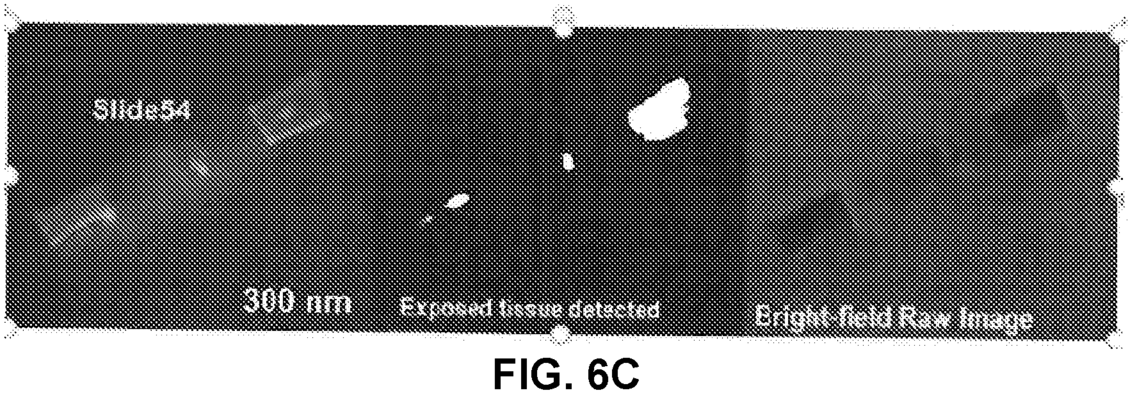
FIG. 6C shows the artificial block illuminated at 300 nm, which exposed tissue detected by the 54th cut. In order to determine the ground truth data an artificial block was created by cutting tissue into a regular shape and measuring it by digital microscopy (cartoon shown in A). The tissue was then re-embedded in paraffin to make an FFPE block (B) that upon microtomy had known parameters for when the tissue is exposed thereby providing ground truth data for algorithm development. In (C), the tissue is illuminated at 300 nm for algorithm development which is indicated by the exposed tissue detected by the $54^{th}$ cut. The brightfield raw image demonstrates the improvement in fluorescence imaging which shows sharply focused tissue and distinguished tissue from paraffin in a superior way.

In order to collect reliable data, an artificial block was created by cutting tissue into an artificial shape and measuring its fluorescence by digital microscopy. FIG. 6A is a cartoon illustration of an artificial block comprising the artificially shaped tissue. FIG. 6B is a photograph of the artificially shaped tissue re-embedded in paraffin to make an artificial FFPE block. Upon microtomy of the artificial block, it will have known parameters for when the tissue is exposed, thereby providing reliable data for algorithm development. In FIG. 6C, the tissue is illuminated at 300 nm for algorithm development which is indicated by the exposed tissue detected by the 54th cut. The brightfield raw image demonstrates the improvement in fluorescence imaging which shows sharply focused tissue and distinguishes tissue from paraffin in a superior way.

EXAMPLE 5

Figure 7A:
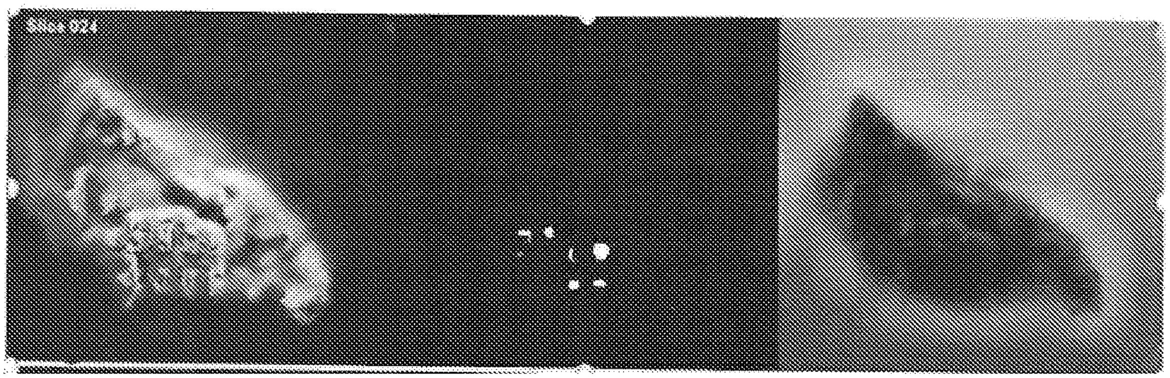
FIGS. 7A to 7C demonstrate performance of the present techniques during automated microtomy of an FFPE block containing lung tissue. Algorithm performance is demonstrated during automated microtomy of an FFPE block containing lung tissue. Fluorescence imaging is shown for the tissue block at wavelengths (300 nm). The center panel indicates the algorithmic-based detection of exposed tissue for the $25^{th}$ five micron slice (1), the $120^{th}$ slice (B) and the $367^{th}$ slice (C). The $24^{th}$ slice had a very little tissue as compared to the deeper cuts into the FFPE block.
Figure 7B:
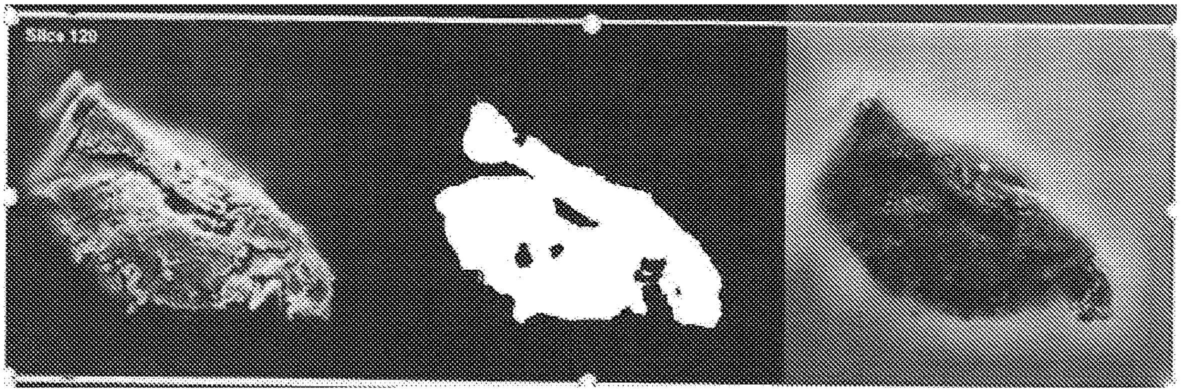
Figure 7C:
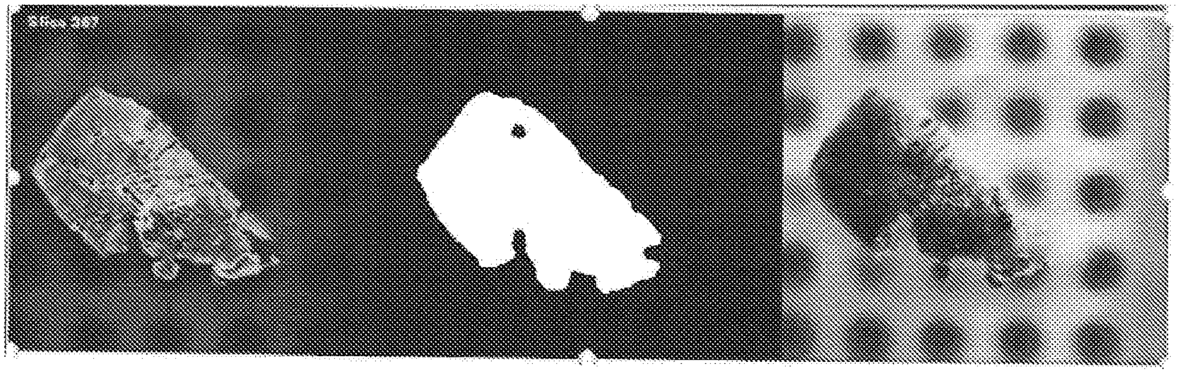

FIGS. 7A to 7C demonstrated performance of the algorithm developed in Example 3 during automated microtomy of an FFPE block containing lung tissue. Fluorescence imaging is shown for the tissue block at wavelengths (300 nm). The center panel indicates the algorithmic-based detection of exposed tissue for the 24th five micron slice (FIG. 7A), the 120th slice (FIG. 7B) and the 367th slice (FIG. 7C). The 24th slice had very little tissue as compared to the deeper cuts into the FFPE block.

EXAMPLE 6

Figures 8A, 8B:
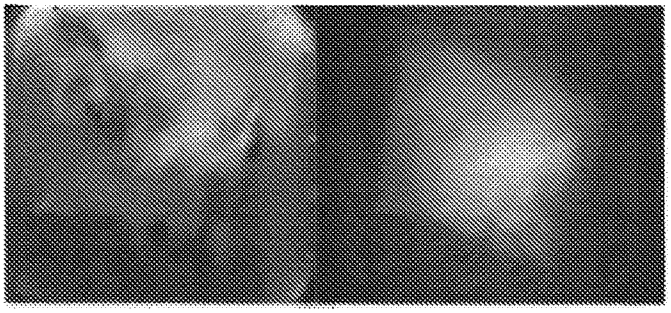
FIGS. 8A and 8B are images of a FFPE tissue block under bright-field and a UV source at 300 nm.
Figures 8C, 8D:
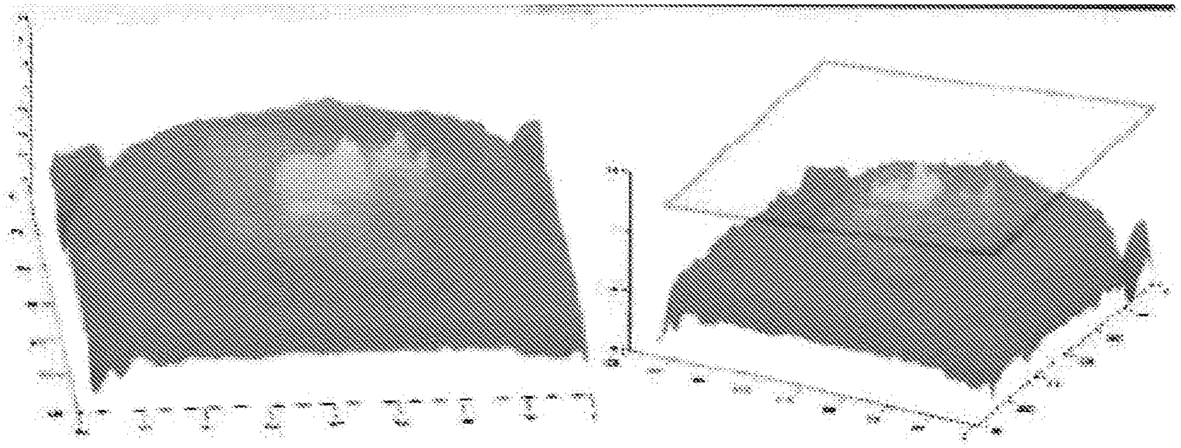
FIG. 8C is an associated depth map showing the topology of the tissue surface with yellow peak indicates the point closest to the block surface and FIG. 8D shows a predicted plane (the mesh plane on the top of the map), generated using the 3D depth map in FIG. 8C, optimal for sectioning the tissue.

To explore which excitation/emission optical bands detects more accurate sub-surface topology of tissue, a fluorescence imaging system was constructed with several LED sources (including 300 nm, 470 nm & white light) and up to six distinct emission filters, arranged in a carousel. The LED sources illuminate the tissue block at different off-axis angles between 45 and 60 degrees from normal incidence. The images in FIGS. 8A and 8B were collected automatically by a 6 megapixel CMOS sensor parallel to the surface of the tissue block before trimming. To improve the image quality, several processing operations, including image registration, CLAHE contrast enhancement, and Gaussian blur, are performed. A depth map of the tissue shown in FIG. 8C is constructed based on the local focus measurement for each pixel. A predicted optimal plane of sectioning to maximize tissue usage shown in FIG. 8D could be calculated based on the tissue topology.

Images of the FFPE tissue block under (FIG. 8A) the bright-field and (FIG. 8B) a UV source at 300 nm. FIG. 8C is an associated depth map showing the topology of tissue surface with yellow as the highest value, indicating that sub-surface topography is evaluable in a low-resolution setup built onto a microtome. FIG. 8D is a predicted optimal plane of sectioning to maximize tissue usage.

EXAMPLE 7

Figure 9:
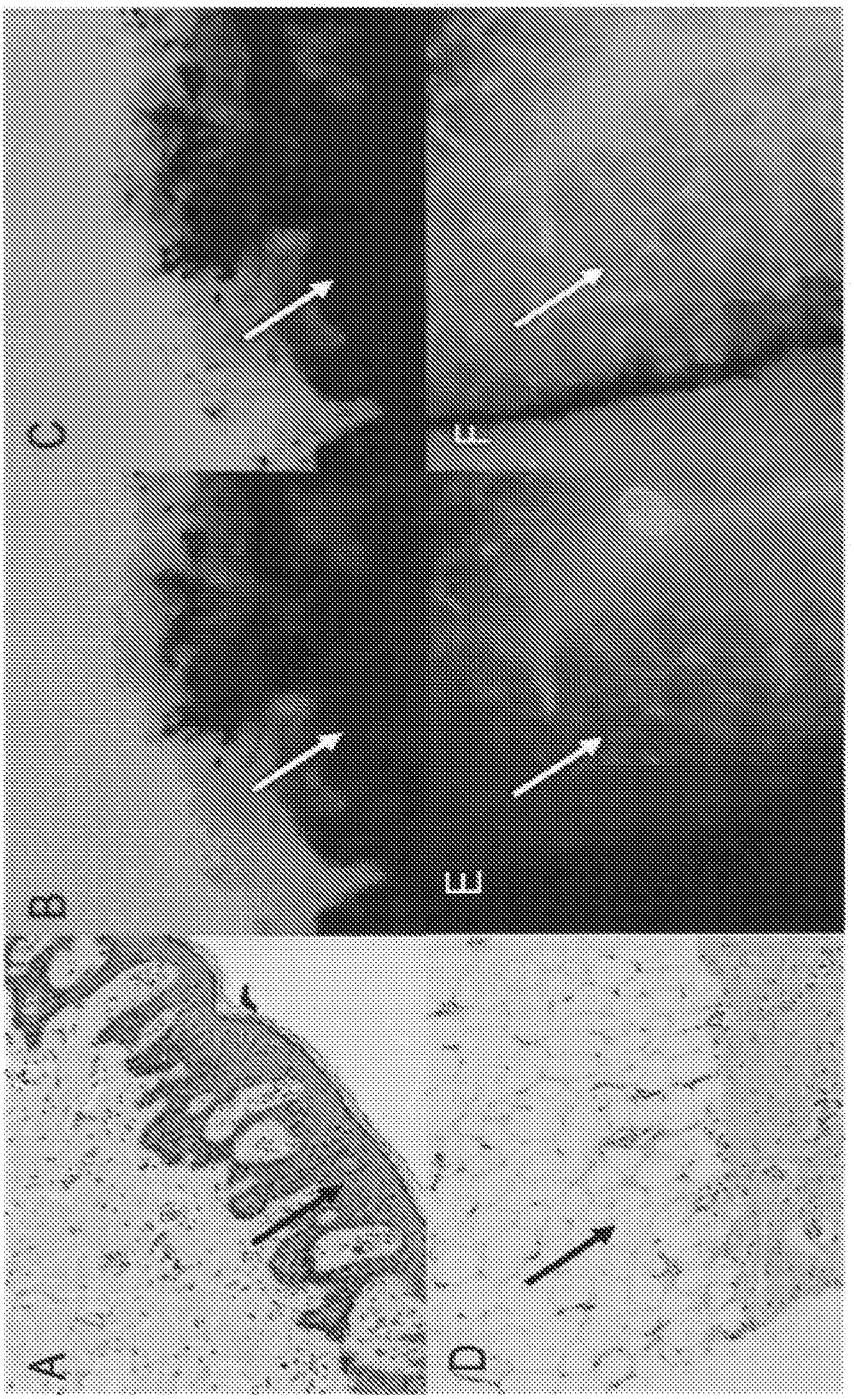
FIGS. 9A-F shows sub-surface topology detection of FFPE tissue using fluorescence-based imaging. High resolution images indicate that autofluorescence imaging distinguishes different cell types in paraffin embedded tissues adding detailed sub-surface topology information to the captured images. Breast tissue was imaged using a filter at 470 nm excitation and 525 nm emission (B and E). Breast tissue was imaged using a filter at 365 nm excitation/445 nm emission (C and F). (A and D) shows images of H&E stained tissue sections of breast tissue with regions of squamous epithelium that are also visible with fluorescence imaging (indicated by arrows in A, B and C) and adipose cells (indicated by arrows in D, E and F). 200× magnification.

FIG. 9 shows sub-surface topology detection of formalin-fixed paraffin embedded tissue using fluorescence-based imaging using the system of Example 6. High resolution images indicate that autofluorescence imaging distinguishes different cell types in paraffin embedded tissues adding detailed sub-surface topology information to the captured images. Breast tissue was imaged using a filter at 470 nm excitation and 525 nm emission (panels B and E). Breast tissue was imaged using a filter at 365 nm excitation/445 nm emission (panels C and F). (panels A and D) shows images of H&E stained tissue sections of breast tissue with regions of squamous epithelium that are also visible with fluorescence imaging (indicated by arrows in panels A, B and C) and adipose cells (indicated by arrows in panels D, E and F). The adipose and squamous epithelium are distinct as compared to the surrounding stroma that appears very bright with fluorescence imaging. 200× magnification.

EXAMPLE 8

This example describes a novel workflow that can be used for (1) algorithm-based detection methods to perform nuclear segmentation for nuclear morphometric analysis, and/or (2) algorithm-based detection methods to perform macrodissection of tumor regions of interest for subsequent genomic testing methods. The algorithms developed using this workflow can be deployed using an unstained FFPE block during microtomy or using a tissue section on a slide. An embodiment of the novel workflow is described in Table 3:

TABLE 3

| Steps | Method | Purpose |
|---|---|---|
| 1 | An FFPE tissue block is imaged during microtomy using autofluorescence | To determine the autofluorescence signature of the tissue embedded in paraffin in the FFPE block |

TABLE 3-continued

| Steps | Method | Purpose |
|---|---|---|
| 2 | Tissue section is mounted onto a slide and scanned using DAPI and FITC filters on a commercial scanner | To determine the location of tumor nuclei, other cell type nuclei and extracellular matrix |
| 3 | Tissue section is deparaffinized and pretreated using traditional xylene and pepsin digestion or e-field treatment with rehydration | To remove residual paraffin and permeabilize the nuclei to DAPI dye |
| 4 | Apply DAPI containing fluorescence mounting media and coverslip section | To dye nuclei blue to add contextual information regarding the FITC autofluorescence of extracellular matrix, collagen and elastins |
| 5 | Scan the tissue section | To provide spatial resolution of nuclei and surrounding extracellular matrix to map to other scans for algorithm development |
| 6 | Remove DAPI mounting media by soaking section in water | To prepare the section for H&E staining |
| 7 | H&E stain and mount coverslips, scan using brightfield imaging | To provide ground truth data to be annotated by a pathologist for algorithm development |
| 8 | Algorithm development | Image registration and mapping of annotations to all scans for nuclear segmentation algorithms and other applications of interest |

Figure 10:
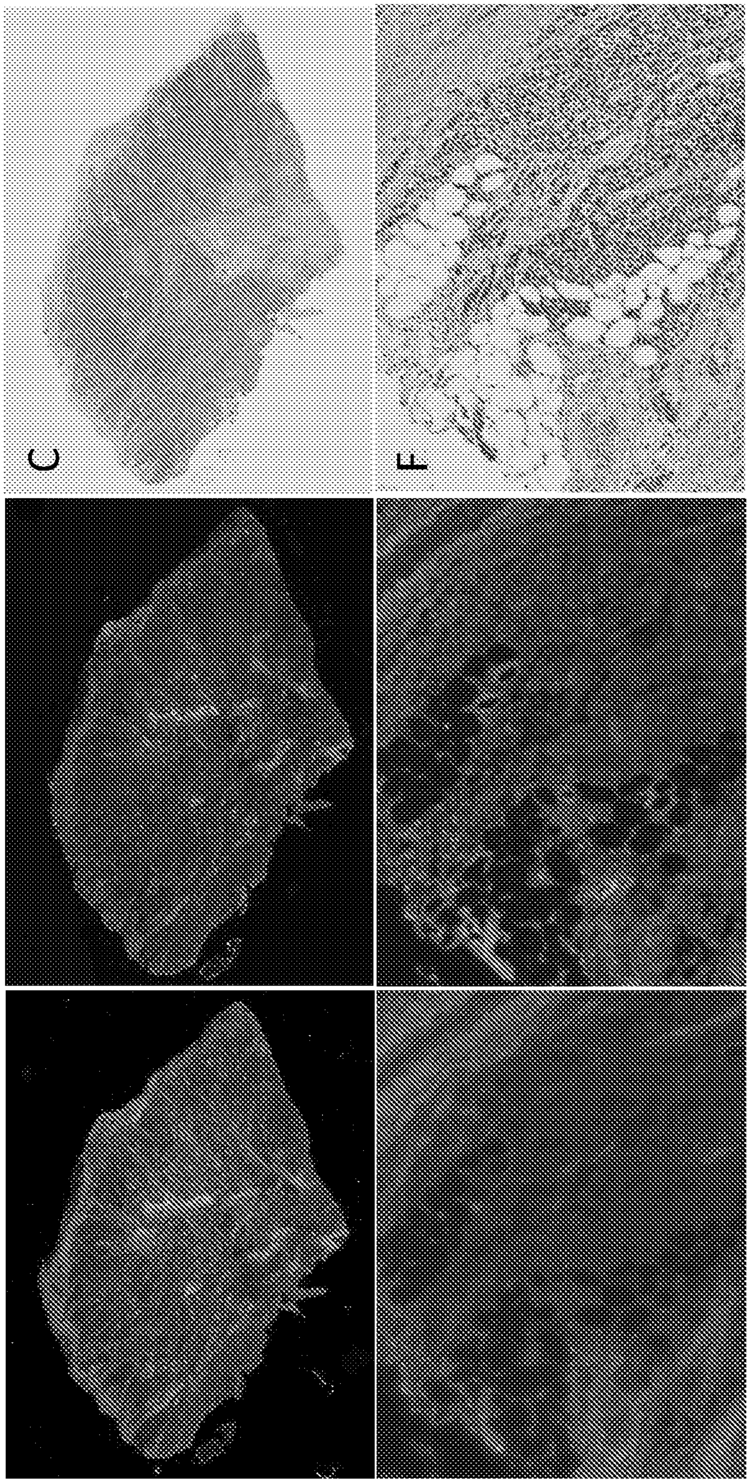
FIGS. 10A-F shows scanned whole-slide-images (WSIs) demonstrating a novel workflow provided by the present disclosure. WSI of autofluorescence imaged unstained deparaffinized FFPE tissue is shown in FIG. 10A and FIG. 10D at 20× magnification. The extracellular matrix is clearly seen in the FITC (green) channel. WSI of fluorescence of DAPI stained tissue in FIG. 10B and FIG. JOE show that the nuclei is clearly discernable from extracellular matrix with the addition of DAPI containing fluorescence mounting media (step 5 of the workflow in Table 3). WSI of the H&E shows the corresponding regions in FIG. 10C and FIG. 10F and show tumor cells, adipose and extracellular matrix (step 7 of the workflow in Table 3).

FIG. 10 shows scanned WSIs demonstrating the workflow. WSI of autofluorescence imaged unstained deparaffinized FFPE tissue are shown in panel A and panel D at 20× magnification. The extracellular matrix is clearly seen in the FITC (green) channel. WSI of fluorescence of DAPI stained tissue panel B and panel E show that the nuclei are clearly discernable from extracellular matrix with the addition of DAPI containing fluorescence mounting media (step 5 of the workflow in Table 1). WSI of the H&E stained tissue of the corresponding regions panel C and panel F show tumor cells, adipose and extracellular matrix (step 7 of the workflow in Table 2).

REFERENCES

Walter et al. US 2010/0118133 A1
Wu et al. US 2019/0188446 A1
Schleifer et al. US 2019/0368982 A1
TissueMark from Philips Computational Pathology
Ramanujam, N., Flourescence Spectroscopy of Neoplastic and Non-Neoplastic Tissues. Neoplasia. 2000 2, 89-117.
Favreau, P. F. et al. Label-free spectroscopic tissue characterization using fluorescence excitation-scanning spectral imaging. J. Biophotonics. 2019; e201900183

EXEMPLARY EMBODIMENTS

Exemplary embodiments provided in accordance with the presently disclosed subject matter include, but are not limited to, the claims and the following embodiments:

Embodiment 1

A method of determining an amount of tissue or cell preparation exposed at a surface of a sample embedded in an embedding medium comprising: irradiating the embedded tissue or cell preparation sample at a wavelength which causes endogenous components of the tissue to autofluoresce; obtaining an image of the autofluorescence emitted by the embedded tissue or cell preparation sample; and determining a percentage of the image at the surface of the embedding medium which is occupied by tissue or cell preparation.

Embodiment 2

The method of embodiment 1, wherein the percentage of the image at the surface of the embedding medium which is occupied by tissue is determined by: slicing a tissue section from the embedded tissue sample, wherein the embedded tissue sample comprises the tissue and the embedding medium; irradiating the embedded tissue sample with electromagnetic radiation having an excitation wavelength; generating a fluorescence image from an autofluorescence emission of the embedded sample; determining a local focus measure for pixels of the fluorescence image; constructing a depth map of the tissue based on evaluating image blur of the fluorescence; and determining a sectioning plane for the embedded sample, based on the depth map.

Embodiment 3

The method of embodiment 2, wherein the local focus measure is determined by applying an operator to the fluorescence image.

Embodiment 4

The method of embodiment 3, wherein the operator is a modified Laplacian operator.

Embodiment 5

The method of embodiment 2 or 3, further comprising performing one or more processing operations to obtain the fluorescence image, wherein at least one of the processing operations is selected from the group consisting of image registration, contrast enhancement, and image smoothing.

Embodiment 6

The method of any of embodiments 2 to 5, wherein the desired amount of tissue within the sectioning plane and a cut tissue section is from 10 to 100% of the maximum cross-sectional area of the tissue within the tissue block Embodiment 7

The method of any of embodiments 2 to 6, wherein the local focus measure is measured in an n-by-n neighborhood surrounding a plurality of pixels in an input image.

Embodiment 8

The method of any of embodiments 2 to 7, wherein the exposed tissue is identified by normalizing a focus metric on each slice image on a first slice image.

Embodiment 9

The method of embodiment 8, wherein the tissue section from the embedded tissue sample will be cut at the sectioning plane when the desired amount of tissue is present.

Embodiment 10

The method of embodiment 9, wherein after the desired amount of tissue is determined, the tissue section from the embedded sample of the sectioning plane is cut.

Embodiment 11

A method of identifying different cell types in an embedded tissue sample comprising: irradiating the embedded tissue sample at a wavelength which causes endogenous components of a tissue to autofluoresce; obtaining an image of the autofluorescence emitted by the tissue sample; and identifying different cell types in the image of the autofluorescence emitted by the tissue sample based upon autofluorescence characteristics.

Embodiment 12

The method of embodiment 11, wherein the different cell types in the embedded tissue sample are determined by: exposing a tissue section from the embedded tissue sample, wherein the embedded tissue sample comprises a tissue and an embedding medium; irradiating the embedded tissue sample with electromagnetic radiation having an excitation wavelength; generating a fluorescence image from autofluorescence emission of the embedded sample; determining a local focus measure for pixels of the fluorescence image; and constructing a depth map of the tissue based on evaluating image blur of the fluorescence.

Embodiment 13

The method of embodiment 12, wherein the fluorescence images are captured by an imaging device.

Embodiment 14

The method of embodiment 12 or 13, wherein the local focus measure is determined by applying an operator to the fluorescence image.

Embodiment 15

The method of embodiment 14, wherein the operator is a modified Laplacian operator.

Embodiment 16

The method of embodiments 12 to 14, further comprising performing one or more processing operations to obtain the fluorescence image, wherein at least one of the processing operations is selected from the group consisting of image registration, contrast enhancement, and image smoothing.

Embodiment 17

The method of any of embodiments 12 to 16, wherein the local focus measure is measured in an n-by-n neighborhood surrounding a plurality of pixels in an input image.

Embodiment 18

The method of any of embodiments 12 to 17, wherein the depth map of the tissue is a subsurface topology of the tissue within the embedding medium.

Embodiment 19

The method of any of embodiments 12 to 18, wherein a predicted optimal plane of sectioning for the tissue sample is based on evaluating the subsurface topology of the tissue within the embedding medium.

Embodiment 20

The method of embodiment 1, wherein the tissue or cell preparation is selected from the group consisting of tissue, cell pellets, and cell spheroids.

Embodiment 21

The method of embodiment 20, wherein the cell spheroids comprise two or more cell types.

Embodiment 22

A method of training an artificial intelligence (AI) system to identify a region of interest (ROI) in an embedded tissue sample comprising a tissue and an embedding medium, wherein the method comprises: irradiating the embedded tissue sample at a wavelength which causes endogenous components of the tissue to autofluoresce; obtaining an image of the autofluorescence emitted by the embedded tissue sample; annotating the image to indicate the ROIs in the image; and inputting the annotated image into the AI system, wherein the AI system learns to identify ROIs in unannotated images.

Embodiment 23

The method of embodiment 22, wherein the AI system comprises at least one of a machine learning system, a deep learning system, a neural network, a convolutional neural network, a fully convolutional neural network, a statistical model-based system, or a deterministic algorithm-based analysis system.

Embodiment 24

The method of embodiment 22, wherein the AI system is a convolutional neural network.

Embodiment 25

The method of embodiment 22, wherein the AI system comprises a segmentation convolutional neural network.

Embodiment 26

The method of embodiment 22, wherein the AI system is a recurrent neural network.

Embodiment 27

The method of embodiment 22 or 26, wherein the embedded tissue sample has been stained with a hematoxylin and eosin (H&E) stain, an immunohistochemistry (IHC) stain, or an immunofluorescence (IF) stain for protein markers.

Embodiment 28

The method of any of embodiments 22 to 27, wherein the image of the embedded tissue sample is annotated on a whole slide image of the embedded tissue sample.

Embodiment 29

The method of any of embodiments 22 to 28, wherein the trained AI system is adapted for identifying a ROI containing tumor cells in accordance with tumor enrichment methods for molecular assays.

Embodiment 30

The method of any of embodiments 22 to 29, wherein the embedded sample is irradiated as part of a tissue block, and the method further comprises slicing the embedded sample from the tissue block as a tissue section.

Embodiment 31

The method of any of embodiments 22 to 30, wherein the AI system learns to identify ROIs in unannotated images by: obtaining an untrained or pretrained AI system; staining the embedded tissue sample with a stain detectable by bright field or fluorescence-based imaging; generating one or more stained images of a stained embedded tissue sample by bright field or fluorescence imaging; annotating the ROI of the stained embedded tissue sample on the one or more stained images; mapping the annotated ROI of the one or more stained images to the unstained autofluorescence image; and training the untrained AI system by using a mapped fluorescence image.

Embodiment 32

The method of embodiment 31, wherein AI system training data is obtained from the mapped autofluorescence image in order to train the untrained or pretrained AI system.

Embodiment 33

The method of any of embodiments 22 to 32, wherein the AI system is adapted for identifying the ROI on an unstained embedded tissue sample.

Embodiment 34

The method of any of embodiments 22 to 33, wherein the ROI identifies tumor containing regions.

Embodiment 35

The method of embodiment 34, wherein the ROI is identified by detecting a fluorescence level corresponding to concentration of endogenous fluorophores from extracellular matrix and cytoplasm surrounding tumor nuclei.

Embodiment 36

The method of embodiment 35, wherein the autofluorescence level of the extracellular matrix and cytoplasm surrounding the tumor nucleus is compared to a autofluorescence level of a control sample.

Embodiment 37

The method of embodiment 36, wherein the control sample comprises a control nucleus, control cytoplasm, control stroma, or control extracellular matrix components.

Embodiment 38

The method of embodiment 36 or 37, wherein the autofluorescence level of the extracellular matrix or cytoplasm surrounding the tumor nucleus is lower than the autofluorescence level of the control sample.

Embodiment 39

The method of embodiment 14, wherein the control nucleus may be smaller than tumor nuclei with fine chromatin and a single nucleolus.

Embodiment 40

The method of embodiment 22, further comprising: mounting the embedded sample as a tissue section onto a slide and imaging the tissues using a first filter and a second filter; treating the tissue section to remove the embedding medium and to permeabilize nuclei to facilitate a stain for nuclei; applying a stain such as DAPI which is specific for nuclei to the tissue section to form a nuclei-stained tissue section; imaging the nuclei-stained tissue section to produce a nuclei-stained tissue section image; removing the nuclei stain mounting medium; applying a hematoxylin and eosin (H&E) stain, an immunohistochemistry (IHC) stain, or an immunofluorescence (IF) stain to produce a cell-stained tissue section; coverslipping the cell-stained tissue section; and imaging the cell-stained tissue section using bright field imaging to produce the stained image.

Embodiment 41

A method of preparing a tissue specimen comprising a region of interest (ROI) from an embedded sample, comprising: obtaining a trained AI system adapted for identifying the ROI from an unstained embedded sample; irradiating the embedded sample comprising a tissue and an embedding medium with electromagnetic radiation having an excitation wavelength; generating a fluorescence image of the embedded sample; using the trained AI system to identify the ROI in the embedded sample based on the fluorescence image and without staining the embedded sample; and collecting a portion of the embedded sample identified as having the ROI as the tissue specimen.

Embodiment 42

The method of embodiment 41, wherein the fluorescence image is generated from a tissue section comprising the embedded sample.

Embodiment 43

The method of embodiment 41, wherein the fluorescence image is generated from a tissue block comprising the embedded sample.

Embodiment 44

The method of embodiment 41, wherein the fluorescence image is generated from a tissue section, and a collected portion of the embedded sample is collected from a tissue block.

Embodiment 45

The method of any of embodiments 41 to 44, wherein the embedding medium is removed from the collected portion of the embedded sample to provide the tissue specimen.

Embodiment 46

The method of embodiment 45, further comprising removing cellular components from the tissue specimen to provide a nucleic acid specimen and determining a nucleic acid sequence from the nucleic acid specimen.

Embodiment 47

The method of any of embodiments 41 to 46, wherein the trained AI system is obtained by: irradiating the embedded tissue sample at a wavelength which causes endogenous components of the tissue to autofluoresce; obtaining an image of the autofluorescence emitted by the embedded tissue sample; annotating the image to indicate the ROIs in the image; and inputting the annotated image into the AI system, wherein the AI system learns to identify ROIs in unannotated images.

Embodiment 48

The method of embodiment 47, wherein the AI system is a convolutional neural network.

Embodiment 49

The method of embodiment 47, wherein the AI system comprises a segmentation convolutional neural network.

Embodiment 50

The method of embodiment 47, wherein the AI system is a recurrent neural network.

Embodiment 51

The method of any of embodiments 41 to 50, wherein the trained AI system is obtained by: imaging the embedded sample as part of the tissue block using autofluorescence and slicing the embedded sample from the tissue block as the tissue section; mounting the embedded sample as the tissue section onto a slide and imaging the tissues using a first filter and a second filter; treating the tissue section to remove the embedding medium and to permeabilize nuclei to a stain for nuclei; applying a nuclei stain in a nuclei stain mounting medium to the tissue section to form a nuclei-stained tissue section; imaging the nuclei-stained tissue section to produce a nuclei-stained tissue section image; removing the nuclei stain mounting medium; applying a hematoxylin and eosin (H&E) stain, an immunohistochemistry (IHC) stain, or an immunofluorescence (IF) stain to produce a cell-stained tissue section; coverslipping the cell-stained tissue section; and imaging the cell-stained tissue section using bright field imaging to produce the stained image.

Embodiment 52

A method of imaging a sample of a biological tissue comprising: irradiating a biological tissue sample at an excitation wavelength which causes endogenous components of the biological tissue to autofluoresce; obtaining an image of the autofluorescence emitted by the biological tissue sample to identify regions of the biological tissue comprising extracellular matrix; and staining nuclei in the biological tissue sample with a nuclear stain to identify regions of the biological tissue comprising cellular nuclei.

Embodiment 53

The method of embodiment 52, wherein the biological tissue sample is deparaffinized and pretreated with a cleaning solution.

Embodiment 54

The method of embodiment 53, wherein the cleaning solution comprises xylene and pepsin digestion or e-field treatment with rehydration.

Embodiment 55

The method of any of embodiments 52 to 54, wherein the nuclear stain contains fluorescent mounting media.

Embodiment 56

The method of any of embodiments 52 to 55, wherein the biological tissue sample is scanned by fluorescence imaging.

Embodiment 57

The method of any of embodiments 52 to 56, wherein the DAPI is removed by soaking the tissue section in water.

Embodiment 58

The method of any of embodiments 52 to 57, wherein a trained AI system is developed.

Embodiment 59

The method of any of embodiments 52 to 58, wherein identifying regions of the biological tissue comprising cellular nuclei allows for identification of tumor cells and nuclear stained tumor cells.

Embodiment 60

The method of any of embodiments 52 to 59, wherein the biological tissue sample is used to develop each autofluorescence image.

Embodiment 61

The method of embodiment 60, wherein the fluorescence image is a first image.

Embodiment 62

The method of embodiment 61, wherein a second image is obtained by staining the nuclei in the biological tissue sample with a nuclear stain.

Embodiment 63

The method of embodiment 62, wherein the first image and the second image identify tumor boundaries in the biological tissues.

Embodiment 64

The method of embodiment 62 or 63, wherein the second image is mapped to an H&E or IHC image in order to show nuclear segmentation of tumor cells.

Embodiment 65

The method of any of embodiments 52 to 64, wherein the regions of the biological tissue comprising cellular nuclei are tumor nuclei.

Embodiment 66

The method of embodiment 65, wherein the regions of the biological tissue comprising cellular nuclei are identified by detecting the autofluorescence level of the extracellular matrix surrounding the tumor nuclei.

Embodiment 67

The method of embodiment 66, wherein the autofluorescence level of the extracellular matrix surrounding the tumor nuclei is compared to an autofluorescence level of a control sample.

Embodiment 68

The method of embodiment 67, wherein the control sample comprises control nuclei, control cytoplasm, control stroma, or control extracellular matrix components.

Embodiment 69

The method of embodiment 68, wherein the fluorescence level of the extracellular matrix surrounding the tumor nuclei is lower than the fluorescence level of the control sample.

Embodiment 70

The method of embodiment 69, wherein the control nuclei are smaller than the tumor nuclei are mono-nucleate, contains one nucleoli and fine chromatin.

In view of this disclosure it is noted that the methods and apparatus can be implemented in keeping with the present teachings. Further, the various components, materials, structures and parameters are included by way of illustration and example only and not in any limiting sense. In view of this disclosure, the present teachings can be implemented in other applications and components, materials, structures and equipment to implement these applications can be determined, while remaining within the scope of the appended claims.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

The term “autofluorescence” refers to the natural emission of light by a biological molecule such as a protein.

The term “fluorophore” refers to a fluorescent compound that can re-emit light upon excitation with light. The term “endogenous fluorophore” refers to a naturally-occurring biological substance capable of autofluorescence.

A “fixed” tissue is one that has been contacted with a fixing agent for a suitable period of time.

An “embedded tissue” or “embedded sample” is a tissue sample that is partially or completely surrounded by an embedding medium such as a paraffin or an epoxy resin. The embedded tissue or embedded sample of the present disclosure should not be confused with a tissue section that results from slicing or trimming of an embedded tissue.

The term “formalin-fixed paraffin-embedded block” or “formalin-fixed paraffin-embedded sample” or “FFPE sample” refers to a formalin-treated tissue embedded in paraffin.

The terms “pixel intensity” or “pixel intensity values” are used interchangeably and refer to the detected fluorescent signal averaged over a region of interest in a digital image. During acquisition of a digital image, the photons that are detected at each pixel are converted to an intensity value that is proportional to the number of detected photons. The pixel intensity can be used to determine the local concentration of fluorophores in a specimen.

As used in the specification and appended claims, and in addition to their ordinary meanings, the terms “substantial” or “substantially” mean to within acceptable limits or degree to one having ordinary skill in the art. For example, “substantially cancelled” means that one skilled in the art considers the cancellation to be acceptable.

As used in the specification and the appended claims and in addition to its ordinary meaning, the terms “approximately” and “about” mean to within an acceptable limit or amount to one having ordinary skill in the art. The term “about” generally refers to plus or minus 15% of the indicated number. For example, “about 10” may indicate a range of 8.5 to 11.5. For example, "approximately the same" means that one of ordinary skill in the art considers the items being compared to be the same.

In the present disclosure, numeric ranges are inclusive of the numbers defining the range. In the present disclosure, wherever the word "comprising" is found, it is contemplated that the words "consisting essentially of" or "consisting of" may be used in its place.

Unless defined otherwise, all technical and scientific terms used herein have the same meaning as commonly understood by those working in the fields to which this disclosure pertain.

All patents and publications referred to herein are expressly incorporated by reference. The citation of any publication is for its disclosure prior to the filing date and should not be construed as an admission that the present claims are not entitled to antedate such publication. Further, the dates of publication provided can be different from the actual publication dates which can be independently confirmed.

As used in the specification and appended claims, the terms "a," "an," and "the" include both singular and plural referents, unless the context clearly dictates otherwise.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

We claim:

1. A method of determining an amount of tissue or cell preparation exposed at a surface of a sample embedded in an embedding medium comprising:

irradiating the embedded tissue or cell preparation sample at a wavelength which causes endogenous components of the tissue to autofluoresce;

obtaining an image of the autofluorescence emitted by the embedded tissue or cell preparation sample; and determining a percentage of the image at the surface of the embedding medium which is occupied by tissue or cell preparation;

wherein the percentage of the image at the surface of the embedding medium which is occupied by tissue is determined by:

slicing a tissue section from the embedded tissue sample, wherein the embedded tissue sample comprises the tissue and the embedding medium;

irradiating the embedded tissue sample with electromagnetic radiation having an excitation wavelength;

generating a fluorescence image from an autofluorescence emission of the embedded sample;

determining a local focus measure for pixels of the fluorescence image;

constructing a depth map of the tissue based on evaluating image blur of the fluorescence; and determining a sectioning plane for the embedded sample, based on the depth map.

2. The method of claim 1, wherein the local focus measure is determined by applying an operator to the fluorescence image.

3. The method of claim 2, wherein the operator is a modified Laplacian operator.

4. The method of claim 1, further comprising performing one or more processing operations to obtain the fluorescence image, wherein at least one of the processing operations is selected from the group consisting of image registration, contrast enhancement, and image smoothing.

5. The method of claim 1, wherein the desired amount of tissue within the sectioning plane and a cut tissue section is from 10 to 100% of the maximum cross-sectional area of the tissue within the tissue block.

6. The method of claim 1, wherein the local focus measure is measured in an n-by-n neighborhood surrounding a plurality of pixels in an input image.

7. The method of claim 1, wherein the exposed tissue is identified by normalizing a focus metric on each slice image on a first slice 1mage.

8. The method of claim 7, wherein the tissue section from the embedded tissue sample will be cut at the sectioning plane when the desired amount of tissue is present.

9. The method of claim 8, wherein after the desired amount of tissue is determined, the tissue section from the embedded sample of the sectioning plane is cut.

10. The method of claim 1, wherein the local focus measure is measured in an n-by-n neighborhood surrounding a plurality of pixels in an input image.

11. The method of claim 10, wherein the depth map of the tissue is a subsurface topology of the tissue within the embedding medium.

* * * * *